(12) United States Patent
Weinstein et al.

(10) Patent No.: US 12,364,401 B2
(45) Date of Patent: Jul. 22, 2025

(54) ARRHYTHMIA MONITORING DEVICE RECONFIGURABLE AS PATCH DEVICE OR HOLSTER DEVICE

(71) Applicant: ZOLL Medical Israel Ltd., Kfar-Saba (IL)

(72) Inventors: Uriel Weinstein, Mazkeret Batya (IL); Arkadi Averboukh, Rehovot (IL); Danny Koifman, Gene Tikva (IL); Rafi Ravid, Savyon (IL); Aviv Rottenberg, Ramat Hasharon (IL); Lior Sela, Kfar-Saba (IL); Leonid Bekman, Holon (IL); David Meshulam, Hod Hasharon (IL)

(73) Assignee: Itamar Medical Ltd., Caesarea (IL)

( * ) Notice: Subject to any disclaimer, the term of this patent is extended or adjusted under 35 U.S.C. 154(b) by 334 days.

(21) Appl. No.: 17/910,409

(22) PCT Filed: Mar. 9, 2021

(86) PCT No.: PCT/IL2021/050261
§ 371 (c)(1),
(2) Date: Sep. 9, 2022

(87) PCT Pub. No.: WO2021/181389
PCT Pub. Date: Sep. 16, 2021

(65) Prior Publication Data
US 2023/0137521 A1 May 4, 2023

Related U.S. Application Data

(60) Provisional application No. 62/988,254, filed on Mar. 11, 2020.

(51) Int. Cl.
*A61B 5/0205* (2006.01)
*A61B 5/00* (2006.01)
(Continued)

(52) U.S. Cl.
CPC ............ *A61B 5/02055* (2013.01); *A61B 5/05* (2013.01); *A61B 5/1116* (2013.01);
(Continued)

(58) Field of Classification Search
CPC ..... A61B 5/02055; A61B 5/05; A61B 5/1116; A61B 5/1118; A61B 5/282; A61B 5/6833; A61B 5/0816; A61B 2562/0219
See application file for complete search history.

(56) References Cited

U.S. PATENT DOCUMENTS 6,605,046 B1   8/2003   Del Mar
8,315,687 B2   11/2012  Cross et al.
(Continued)

*Primary Examiner* — Mallika D Fairchild
(74) *Attorney, Agent, or Firm* — The Webb Law Firm

(57) ABSTRACT

A patient monitoring system for use in either a patch mode or a holster mode for monitoring physiological data of a patient includes a multi-mode sensor configured to continuously and/or intermittently acquire the physiological data from the patient in the least two modes and to transmit the acquired physiological data to a remote location and/or record the acquired physiological data in an internal memory, the physiological data including one or more of patient electrocardiogram (ECG) data, patient posture, patient movement, radio-frequency (RF) based physiological data, body temperature, and/or patient respiration; an attachment mechanism disposed on the multi-mode sensor, the attachment mechanism configured to removably connect the multi-mode sensor to either a holster and associated monitoring cables worn by the patient or a patch worn by the patient; at least one electrical contact disposed on the multi-mode sensor, the at least one electrical contact configured to engage a counterpart electrical contact of the holster and/or a counterpart electrical contact of the patch; and configuration circuitry disposed in the multi-mode sensor. The configuration circuitry is configured to determine when the multi-mode sensor is removably connected to the (Continued)

holster and cause the multi-mode sensor to acquire the physiological data in the holster mode when connected to the holster, and to determine when the multi-mode sensor is removably connected to the patch and cause the multi-mode sensor to acquire the physiological data in the patch mode when connected to the patch.

19 Claims, 23 Drawing Sheets

(51) Int. Cl.
*A61B 5/05* (2021.01)
*A61B 5/08* (2006.01)
*A61B 5/11* (2006.01)
*A61B 5/282* (2021.01)
*A61B 5/333* (2021.01)

(52) U.S. Cl.
CPC ............ *A61B 5/1118* (2013.01); *A61B 5/282* (2021.01); *A61B 5/333* (2021.01); *A61B 5/6833* (2013.01); *A61B 5/0816* (2013.01); *A61B 2562/0219* (2013.01)

(56) References Cited

U.S. PATENT DOCUMENTS

| | | | |
|---|---|---|---|
| 9,545,212 B2 | 1/2017 | Kim | |
| 2009/0069642 A1 | 3/2009 | Gao et al. | |
| 2010/0298661 A1* | 11/2010 | McCombie | G08B 21/0446 600/587 |
| 2011/0021937 A1* | 1/2011 | Hugh | A61B 5/0205 600/523 |
| 2012/0283794 A1 | 11/2012 | Kaib et al. | |
| 2014/0051946 A1 | 2/2014 | Arne et al. | |
| 2017/0296093 A1* | 10/2017 | Ravid | A61B 5/0816 |
| 2019/0046038 A1 | 2/2019 | Weinstein et al. | |
| 2019/0059757 A1* | 2/2019 | Balda | A61B 5/1116 |
| 2019/0131742 A1* | 5/2019 | Veenstra | G01D 21/00 |

* cited by examiner

ARRHYTHMIA MONITORING DEVICE RECONFIGURABLE AS PATCH DEVICE OR HOLSTER DEVICE

CROSS REFERENCE TO RELATED APPLICATIONS

This application is the United States national phase of International Application No. PCT/IL2021/050261, filed Mar. 9, 2021, and claims priority to U.S. Provisional Patent Application No. 62/988,254, filed Mar. 11, 2020, the disclosures each of which are hereby incorporated by reference in their entireties.

FIELD OF THE DISCLOSURE

The present disclosure relates to examples of systems, devices, and methods for physiological monitoring of patients, and more particularly to systems, devices, and methods for physiological monitoring of patients having different modes of use.

BACKGROUND OF THE DISCLOSURE

There is a wide variety of electronic and mechanical devices for monitoring underlying patients' medical conditions. In some examples, depending on the underlying medical condition being monitored and/or treated, medical devices such as cardiac pacemakers or defibrillators may be surgically implanted or connected externally to the patient. Physicians may use such devices alone or in combination with drug therapies to treat or control patient medical conditions.

Such patients can include heart failure patients; e.g., congestive heart failure (CHF) is a condition in which the heart's function as a pump is inadequate to meet the body's needs. Generally, many disease processes can impair the pumping efficiency of the heart to cause congestive heart failure. The symptoms of congestive heart failure vary, but can include: fatigue, diminished exercise capacity, shortness of breath, and swelling (edema). The diagnosis of congestive heart failure is based on knowledge of the individual's medical history, a careful physical examination, and selected laboratory tests.

Patients in this group can suffer from cardiac arrhythmias. One of the most deadly cardiac arrhythmias is ventricular fibrillation (VF), which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. Yet other cardiac arrhythmias include atrial flutter, heart pauses, ventricular tachycardia (VT), heart block (e.g., of several types), supraventricular tachycardia (SVT), ventricular runs, ventricular bigeminy, junctional rhythm, atrial run, and atrial bigeminy. External pacemakers, defibrillators, and other medical monitors designed for ambulatory and/or long-term use have further improved the ability to detect and treat life-threatening conditions in a timely manner.

Heart failure patients can also benefit from having their thoracic fluid levels being monitored. Radio-frequency (RF) electromagnetic radiation has been used for diagnosis and imaging of body tissues. Diagnostic devices that include an antenna can be used to direct the RF electromagnetic waves into a body and generate signals responsively to the waves that are scattered from within the body. Such signals can be processed to determine various properties of body tissues located along the paths of the transmitted and/or scattered RF waves.

SUMMARY OF SOME OF THE EMBODIMENTS

Non-limiting examples of some of the embodiments will now be described.

Examples of the current disclosure include a patient monitoring system for use in either a patch mode or a holster mode for monitoring physiological data of a patient, comprising: a multi-mode sensor configured to continuously and/or intermittently acquire the physiological data from the patient in the least two modes and to transmit the acquired physiological data to a remote location and/or record the acquired physiological data in an internal memory, the physiological data comprising one or more of patient electrocardiogram (ECG) data, patient posture, patient movement, radio-frequency (RF) based physiological data, body temperature, and/or patient respiration; an attachment mechanism disposed on the multi-mode sensor, the attachment mechanism configured to removably connect the multi-mode sensor to either a holster and associated monitoring cables worn by the patient or a patch worn by the patient; at least one electrical contact disposed on the multi-mode sensor, the at least one electrical contact configured to engage a counterpart electrical contact of the holster and/or a counterpart electrical contact of the patch; and configuration circuitry disposed in the multi-mode sensor. The configuration circuitry is configured to: determine when the multi-mode sensor is removably connected to the holster, and cause the multi-mode sensor to acquire the physiological data in the holster mode when connected to the holster; and determine when the multi-mode sensor is removably connected to the patch, and cause the multi-mode sensor to acquire the physiological data in the patch mode when connected to the patch.

In some examples, the system further comprises the holster, the holster configured to removably receive the multi-mode sensor. The holster may comprise a user interface element configured to be actuated by the patient. The user interface element may comprise a symptom report button. The symptom report button, on actuation, may cause the multi-mode sensor to generate an event report at a time when the symptom report button is actuated.

The holster may comprise a connection mechanism configured to removably connect the holster to the patient. The connection mechanism may comprise at least one of: a clip, a neck lanyard, a magnetic coupling, and/or a strap.

In some examples, the system further comprises the associated monitoring cables, the associated monitoring cables comprising a plurality of separate cables comprising distal and opposing ends. The system may further comprise a plurality of ECG electrodes corresponding to the plurality of separate cables, each of the plurality of ECG electrodes being disposed at a distal end of a corresponding cable and configured to be releasably attached to the patient's skin. The system may further comprise a connector mechanically coupled to the opposing ends of the plurality of separate cables; and a main monitoring cable comprising a connector end coupled to the connector and a holster end configured to be releasably connected to the holster. The holster may comprise a receiver configured to releasably receive the holster end of the monitoring cable. The plurality of ECG electrodes may comprise at least two ECG electrodes configured to sense ECG signals of the patient when attached to the patient's skin, and the patient monitoring system is configured to provide at least one ECG channel based on the at least two ECG electrodes. The at least two ECG electrodes may comprise three ECG electrodes, and the at least one ECG channels may comprise three ECG channels. Each of the distal ends of the plurality of separate cables may comprise an accelerometer and associated circuitry, and the multi-mode sensor may be configured to monitor for at least one of: patient posture, patient movement, and/or patient respiration, based on accelerometer data.

In some examples, the system further comprises the patch, the patch comprising: an adhesive layer; a fabric base configured to be removably attached to the patient's skin via the adhesive layer; a housing configured to removably receive the multi-mode sensor disposed on the fabric base; and a plurality of ECG electrodes disposed in or on the fabric base, the plurality of ECG electrodes configured to detect ECG signals of the patient. The plurality of ECG electrodes disposed in or on the fabric base may comprise two ECG electrodes. The patch may be configured to be continuously worn by the patient for an extended period of time. The extended period of time may comprise a period of between around 6 hours and around 5 days. The extended period of time may comprise a period of between around 6 hours and around 10 days. The extended period of time may comprise a period of between around 3 days and around 30 days. The extended period of time may comprise a period of between around 3 days and around 60 days. The extended period of time may comprise a period of between around 3 days and around 90 days.

In some examples, the multi-mode sensor further comprises at least one radio-frequency (RF) antenna disposed on a patient-facing side of the multi-mode sensor, the at least one RF antenna being configured to transmit RF waves from the multi-mode sensor into the patient and to receive reflected RF waves from the patient.

In some examples, the attachment mechanism may form a snap connection between the multi-mode sensor and the holster or the patch. The attachment mechanism may comprise a pivotable latch disposed on the multi-mode sensor, the pivotable latch configured to engage a corresponding catch formed on the holster or on the patch. The attachment mechanism may comprise at least one rib disposed on the multi-mode sensor, the at least one rib configured to be received in a corresponding recess defined in the holster or on the patch.

In some examples, the at least one electrical contact of the multi-mode sensor comprises a plurality of electrical contacts. The plurality of electrical contacts comprises at least one electrical contact configured to communicate ECG data, at least one electrical contact configured to communicate accelerometer data, and at least one electrical contact configured to transmit power. The plurality of electrical contacts may further comprise at least one electrical contact configured to transmit an RF signal and/or communicate RF-based physiological data.

In some examples, the configuration circuitry comprises resistance detection circuitry configured to detect a resistance level between the at least one electrical contact of the multi-mode sensor and the counterpart electrical contact of the holster or the counterpart electrical contact of the patch, the configuration circuitry being configured to determine when the multi-mode sensor is removably connected to the holster or the patch based on the detected resistance level.

In some examples, the multi-mode sensor comprises communications circuitry configured to transmit the acquired physiological data to the remote location via a local communications gateway.

In some examples, the multi-mode sensor comprises communications circuitry configured to transmit the acquired physiological data to the remote location via a cellular telecommunications signal.

In some examples, the multi-mode sensor comprises an accelerometer and associated circuitry and is configured to monitor for at least one of: patient posture, patient movement, and/or patient respiration, based on accelerometer data.

In some examples, the multi-mode sensor comprises ECG circuitry configured to communicate with at least one ECG channel and continuously acquire ECG data from the patient. The physiological data may comprise ECG data, and the ECG circuitry may be configured to acquire the ECG data from the patient via the at least one ECG channel when in the patch mode. The physiological data may comprise ECG data, and the ECG circuitry may be configured to acquire the ECG data from the patient via at least two ECG channels when in the holster mode.

In some examples, the physiological data comprises RF-based physiological data, and the multi-mode sensor comprises RF circuitry configured to acquire the RF-based physiological data from the patient when in the patch mode.

In some examples, the multi-mode sensor is configured to detect a disconnect between the holster and the monitoring cables and/or the monitoring cables and the patient when in the holster mode.

In some examples, the multi-mode sensor is configured to transmit ECG data based on one or more ECG channels to the remote location.

In some examples, the multi-mode sensor is configured to transmit RF-based physiological data to the remote location.

In some examples, the configuration circuitry is configured to determine when the multi-mode sensor is removably connected to a garment and cause the multi-mode sensor to acquire the physiological data in a garment mode when connected to the garment.

On some examples, the configuration circuitry is configured to determine when the multi-mode sensor is removably connected to a charger device and cause the battery of the multi-mode sensor to be charged.

In some examples, the multi-mode sensor comprises diagnostic circuitry configured to detect a physiological condition of the patient based on the acquired physiological data. The acquired physiological data that may be used to detect the physiological condition comprises patient ECG data. The detected physiological condition may be a cardiac arrhythmia.

Preferred and non-limiting embodiments or aspects of the present disclosure will now be described in the following numbered clauses:

Clause 1. A patient monitoring system for use in either a patch mode or a holster mode for monitoring physiological data of a patient, comprising: a multi-mode sensor configured to continuously and/or intermittently acquire the physiological data from the patient in the least two modes and to transmit the acquired physiological data to a remote location and/or record the acquired physiological data in an internal memory, the physiological data comprising one or more of patient electrocardiogram (ECG) data, patient posture, patient movement, radio-frequency (RF) based physiological data, body temperature, and/or patient respiration; an attachment mechanism disposed on the multi-mode sensor, the attachment mechanism configured to removably connect the multi-mode sensor to either a holster and associated monitoring cables worn by the patient or a patch worn by the patient; at least one electrical contact disposed on the multi-mode sensor, the at least one electrical contact configured to engage a counterpart electrical contact of the holster and/or a counterpart electrical contact of the patch; and configuration circuitry disposed in the multi-mode sensor, the configuration circuitry configured to: determine when the multi-mode sensor is removably connected to the holster, and cause the multi-mode sensor to acquire the physiological data in the holster mode when connected to the holster; and determine when the multi-mode sensor is removably connected to the patch, and cause the multi-mode sensor to acquire the physiological data in the patch mode when connected to the patch.

Clause 2. The patient monitoring system according to clause 1, further comprising the holster, the holster configured to removably receive the multi-mode sensor.

Clause 3. The patient monitoring system according to clause 2, wherein the holster comprises user interface element configured to be actuated by the patient.

Clause 4. The patient monitoring system according to clause 3, wherein the user interface element comprises a symptom report button.

Clause 5. The patient monitoring system according to clause 4, wherein the symptom report button, on actuation, causes the multi-mode sensor to generate an event report at a time when the symptom report button is actuated.

Clause 6. The patient monitoring system according to any one of clauses 2-5, wherein the holster comprises a connection mechanism configured to removably connect the holster to the patient.

Clause 7. The patient monitoring system according to clause 6, wherein the connection mechanism comprises at least one of: a clip, a neck lanyard, a magnetic coupling, and/or a strap.

Clause 8. The patient monitoring system according to any one of clauses 1-7, further comprising the associated monitoring cables, the associated monitoring cables comprising a plurality of separate cables comprising distal and opposing ends.

Clause 9. The patient monitoring system according to clause 8, further comprising a plurality of ECG electrodes corresponding to the plurality of separate cables, each of the plurality of ECG electrodes being disposed at a distal end of a corresponding cable and configured to be releasably attached to the patient's skin.

Clause 10. The patient monitoring system according to clause 9, further comprising: a connector mechanically coupled to the opposing ends of the plurality of separate cables; and a main monitoring cable comprising a connector end coupled to the connector and a holster end configured to be releasably connected to the holster.

Clause 11. The patient monitoring system according to clause 10, wherein the holster comprises a receiver configured to releasably receive the holster end of the monitoring cable.

Clause 12. The patient monitoring system according to any one of clauses 9-11, wherein the plurality of ECG electrodes comprises at least two ECG electrodes configured to sense ECG signals of the patient when attached to the patient's skin, and the patient monitoring system is configured to provide at least one ECG channel based on the at least two ECG electrodes.

Clause 13. The patient monitoring system according to clause 12, wherein the at least two ECG electrodes comprise three ECG electrodes, and the at least one ECG channel comprises three ECG channels.

Clause 14. The patient monitoring system according to any one of clauses 8-13, wherein each of the distal ends of the plurality of separate cables comprises an accelerometer and associated circuitry and the multi-mode sensor is configured to monitor for at least one of: patient posture, patient movement, and/or patient respiration, based on accelerometer data.

Clause 15. The patient monitoring system according to any one clauses 1-14, further comprising the patch, the patch comprising: an adhesive layer; a fabric base configured to be removably attached to the patient's skin via the adhesive layer; a housing configured to removably receive the multi-mode sensor disposed on the fabric base; and a plurality of ECG electrodes disposed in or on the fabric base, the plurality of ECG electrodes configured to detect ECG signals of the patient.

Clause 16. The patient monitoring system according to clause 15, wherein the plurality of ECG electrodes disposed in or on the fabric base comprises two ECG electrodes.

Clause 17. The patient monitoring system according to clause 15 or clause 16, wherein the patch is configured to be continuously worn by the patient for an extended period of time.

Clause 18. The patient monitoring system according to clause 17, wherein the extended period of time comprises a period of between around 6 hours and around 5 days.

Clause 19. The patient monitoring system according to clause 17 or clause 18, wherein the extended period of time comprises a period of between around 6 hours and around 10 days.

Clause 20. The patient monitoring system according to any one of clauses 17-19, wherein the extended period of time comprises a period of between around 3 days and around 30 days.

Clause 21. The patient monitoring system according to any one of clauses 17-20, wherein the extended period of time comprises a period of between around 3 days and around 60 days.

Clause 22. The patient monitoring system according to any one of clauses 17-21, wherein the extended period of time comprises a period of between around 3 days and around 90 days.

Clause 23. The patient monitoring system according to any one of clauses 1-22, wherein the multi-mode sensor further comprises at least one radio-frequency (RF) antenna disposed on a patient-facing side of the multi-mode sensor, the at least one RF antenna being configured to transmit RF waves from the multi-mode sensor into the patient and to receive reflected RF waves from the patient.

Clause 24. The patient monitoring system according to any one of clauses 1-23, wherein the attachment mechanism forms a snap connection between the multi-mode sensor and the holster or the patch.

Clause 25. The patient monitoring system according to any one of clauses 1-24, wherein the attachment mechanism comprises a pivotable latch disposed on the multi-mode sensor, the pivotable latch configured to engage a corresponding catch formed on the holster or on the patch.

Clause 26. The patient monitoring system according to any one of clauses 1-25, wherein the attachment mechanism comprises at least one rib disposed on the multi-mode sensor, the at least one rib configured to be received in a corresponding recess defined in the holster or on the patch.

Clause 27. The patient monitoring system according to any one of clauses 1-26, wherein the at least one electrical contact of the multi-mode sensor comprises a plurality of electrical contacts.

Clause 28. The patient monitoring system according to clause 27, wherein the plurality of electrical contacts comprises at least one electrical contact configured to communicate ECG data, at least one electrical contact configured to communicate accelerometer data, and at least one electrical contact configured to transmit power.

Clause 29. The patient monitoring system according to clause 28, wherein the plurality of electrical contacts further comprises at least one electrical contact configured to transmit an RF signal and/or communicate RF-based physiological data.

Clause 30. The patient monitoring system according to any one of clauses 1-29, wherein the configuration circuitry comprises resistance detection circuitry configured to detect a resistance level between the at least one electrical contact of the multi-mode sensor and the counterpart electrical contact of the holster or the counterpart electrical contact of the patch, the configuration circuitry being configured to determine when the multi-mode sensor is removably connected to the holster or the patch based on the detected resistance level.

Clause 31. The patient monitoring system according to any one of clauses 1-30, wherein multi-mode sensor comprises communications circuitry configured to transmit the acquired physiological data to the remote location via a local communications gateway.

Clause 32. The patient monitoring system according to any one of clauses 1-31, wherein the multi-mode sensor comprises communications circuitry configured to transmit the acquired physiological data to the remote location via a cellular telecommunications signal.

Clause 33. The patient monitoring system according to any one of clauses 1-32, wherein the multi-mode sensor comprises an accelerometer and associated circuitry and is configured to monitor for at least one of: patient posture, patient movement, and/or patient respiration, based on accelerometer data.

Clause 34. The patient monitoring system according to any one of clauses 1-33, wherein the multi-mode sensor comprises ECG circuitry configured to communicate with at least one ECG channel and continuously acquire ECG data from the patient.

Clause 35. The patient monitoring system according to clause 34, wherein the physiological data comprises ECG data, and the ECG circuitry is configured to acquire the ECG data from the patient via the at least one ECG channel when in the patch mode.

Clause 36. The patient monitoring system according to clause 34 or clause 35, wherein the physiological data comprises ECG data, and the ECG circuitry is configured to acquire the ECG data from the patient via at least two ECG channels when in the holster mode.

Clause 37. The patient monitoring system according to any one of clauses 1-36, wherein the physiological data comprises RF-based physiological data, and the multi-mode sensor comprises RF circuitry configured to acquire the RF-based physiological data from the patient when in the patch mode.

Clause 38. The patient monitoring system according to any one of clauses 1-37, wherein the multi-mode sensor is configured to detect a disconnect between the holster and the monitoring cables and/or the monitoring cables and the patient when in the holster mode.

Clause 39. The patient monitoring system according to any one of clauses 1-38, wherein the multi-mode sensor is configured to transmit ECG data based on one or more ECG channels to the remote location.

Clause 40. The patient monitoring system according to any one of clauses 1-39, wherein the multi-mode sensor is configured to transmit RF-based physiological data to the remote location.

Clause 41. The patient monitoring system according to any one of clauses 1-40, wherein the configuration circuitry is configured to determine when the multi-mode sensor is removably connected to a garment, and cause the multi-mode sensor to acquire the physiological data in a garment mode when connected to the garment.

Clause 42. The patient monitoring system according to any one of clauses 1-41, wherein the configuration circuitry is configured to determine when the multi-mode sensor is removably connected to a charger device, and cause the battery of the multi-mode sensor to be charged.

Clause 43. The patient monitoring system according to any one clauses 1-42, wherein the multi-mode sensor comprises diagnostic circuitry configured to detect a physiological condition of the patient based on the acquired physiological data.

Clause 44. The patient monitoring system according to clause 43, wherein the acquired physiological data used to detect the physiological condition comprises patient ECG data.

Clause 45. The patient monitoring system according to clause 44, wherein the detected physiological condition is a cardiac arrhythmia.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings.

DETAILED DESCRIPTION OF SOME OF THE EMBODIMENTS

Figure 1A:
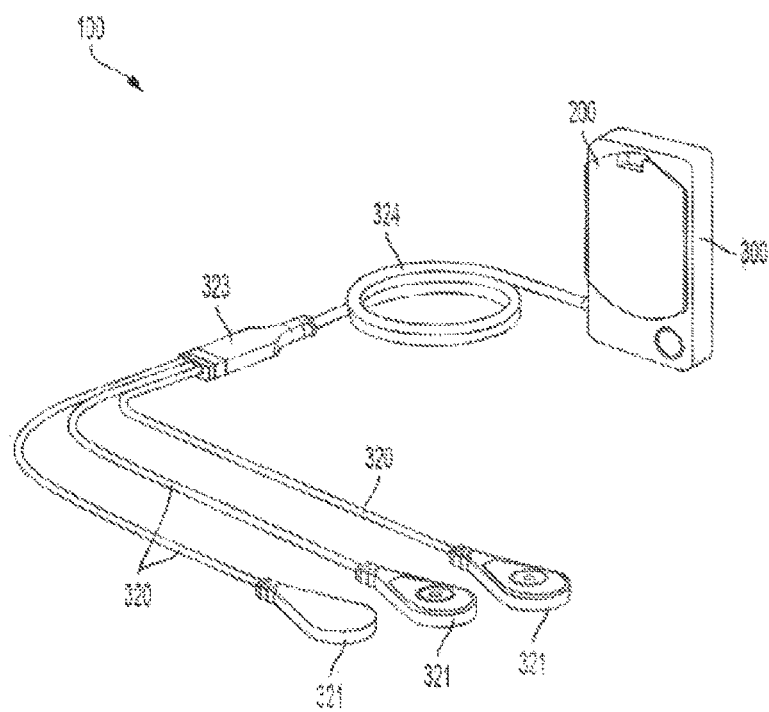
FIG. 1A is a perspective view of a patient monitoring system in a first possible mode of use according to an example of the present disclosure.

As used herein, the singular forms of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings and described in the following specification are examples. Hence, specific dimensions and other physical characteristics related to the embodiments disclosed herein are not to be considered as limiting.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Also, it should be understood that any numerical range recited herein is intended to include all subranges subsumed therein. For example, a range of "1 to 10" is intended to include any and all subranges between and including the recited minimum value of 1 and the recited maximum value of 10; that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible.

Medical professionals can use the systems, apparatus, and techniques described herein for monitoring of vital signs such as ECG, thoracic fluid status, heart rate, respiration rate, temperature, blood pressure, and oxygen saturation to assess their patients' clinical status. Assessing and managing a patient's clinical status involves an integrated approach and is based on assessment of several parameters in addition to those derived from the technology described herein; e.g., clinical observations/assessment, weight loss/gain, urine output, radiographic signs, among others. In examples, devices and techniques herein are configured to monitor for normal respiration rate ranges; e.g., from 10 to 20 breaths per minute, in accordance with standard of care, and changes and/or deviations from this normal range are part of the patient clinical assessment. The availability of such a device, system and/or method for health care professionals to remotely and wirelessly monitor these parameters hence provides a useful role in the care of patients.

Applicant has developed microwave imaging technology. For example, Applicant's technology makes use of a non-ionizing technique by illuminating the body with low-power electromagnetic pulses at RF (radio-frequency) Microwave frequencies (e.g., 0.2-3 GHz) and measuring the returned signals. The reflected and refracted radar signals enable the system to discern between different tissues based on their electromagnetic properties. Such RF-based monitoring can be performed on a continuous and/or an intermittent basis. Applicant has also developed ECG monitoring technology for continuous and/or intermittent monitoring of ECG metrics for cardiac abnormalities such as dysrhythmias and/or changes in an underlying ECG rhythm for advanced monitoring. Such technologies can be provided to caregivers to enhance their abilities to monitor cardiac patients and improve standard of care. For example, in heart failure patient populations or post-myocardial infarction populations, such technologies can provide caregivers with the necessary tools to aid and monitor the progress of their patients' care. While example implementations described herein may reference heart failure patients and their underlying conditions, it is appreciated that the principles herein relate to cardiac diagnosis based on ECG analysis, including for ambulatory and/or outpatient diagnosis based on ECG analysis, such as mobile cardiac telemetry (MCT), cardiac event monitoring (CEM) or holster (e.g., long- or short-term) monitoring of patients.

In some embodiments, the systems, devices, and methods related to the wearable and/or wireless multi-mode sensor(s) disclosed herein can be used to aid clinicians in the diagnosis and identification of various clinical conditions, events and/or trends. In various implementations described in detail below, the systems, devices, and methods aid in the continuous detection and monitoring of cardiac related conditions, such as arrhythmias. Alternatively or additionally, systems, devices, and methods herein aid in continuous and/or intermittent or periodic monitoring of tissue fluid levels such as thoracic fluid content (TFC) levels, including trends relating to these conditions. The arrhythmia and/or fluid monitoring system disclosed herein comprises a multi-mode sensor device that contains one or more of a radar transceiver for carrying out radio-frequency measurements relating to TFC levels of a patient, one or more tri-axis accelerometers, and an ECG monitor (e.g., single lead or multiple lead), and is configured to monitor various health parameters of the patient wearing the sensor(s) including lung/thoracic fluid content levels, heart rate, heart arterial pulse motion, respiration rate, posture, movement and activity level, arrhythmia events, body temperature, and/or the like.

Figure 1B:
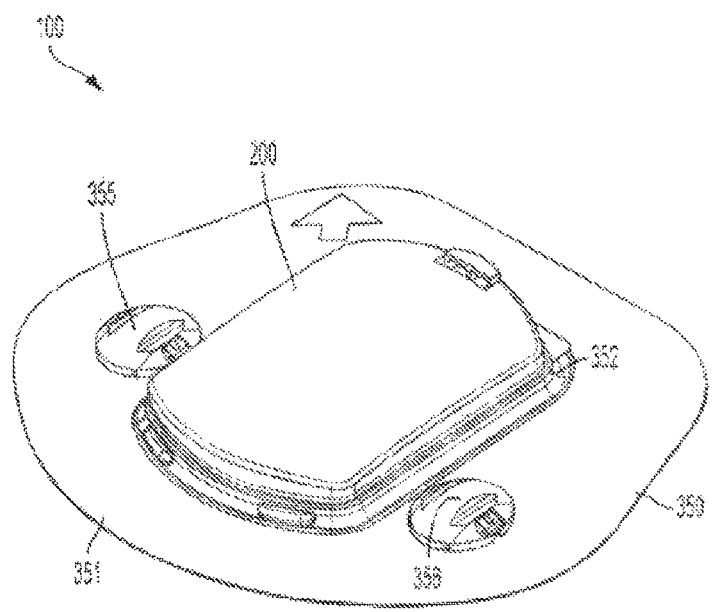
FIG. 1B is a perspective view of the patient monitoring system in a second possible mode of use according to an example of the present disclosure.
Figure 1C:
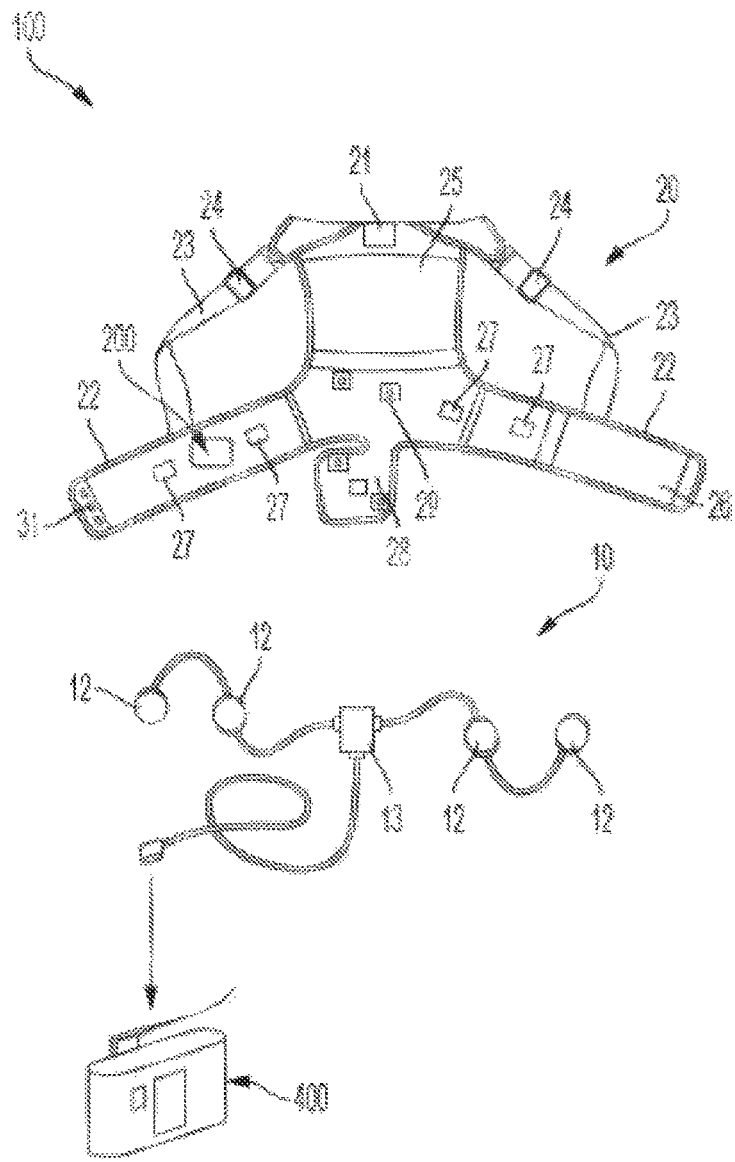
FIG. 1C is a schematic illustration of the patient monitoring system in a third possible mode of use according to an example of the present disclosure.
Figure 2A:
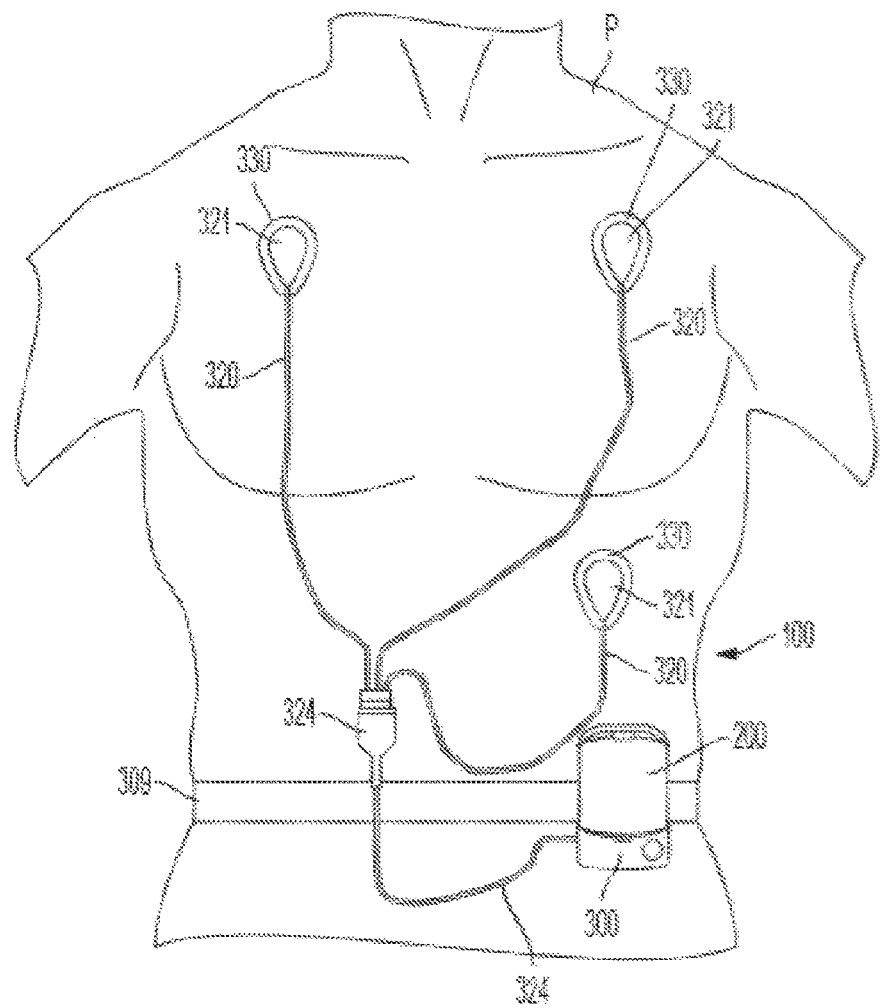
FIG. 2A is a schematic illustration of the patient monitoring system of FIG. 1A worn by a patient in an example configuration of the first possible mode of use.
Figure 2B:
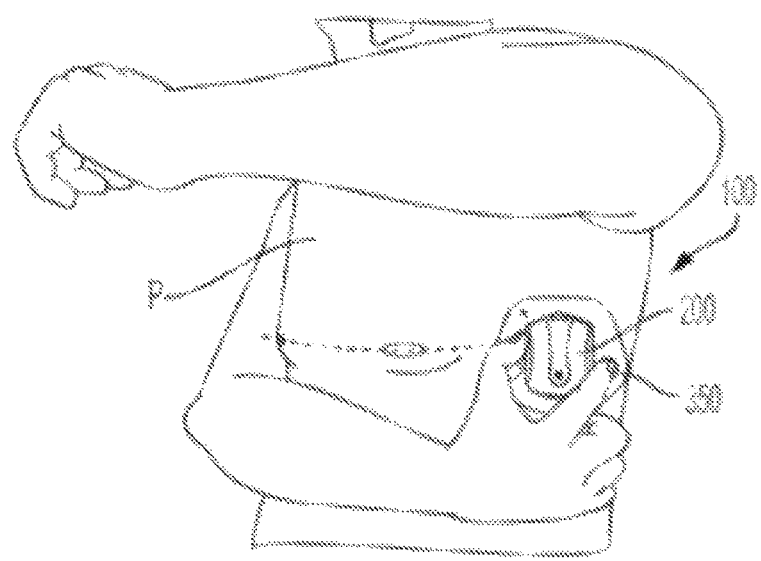
FIG. 2B is a schematic representation of the patient monitoring system of FIG. 1B worn by the patient in an example configuration in the second possible mode of use.
Figure 2C:
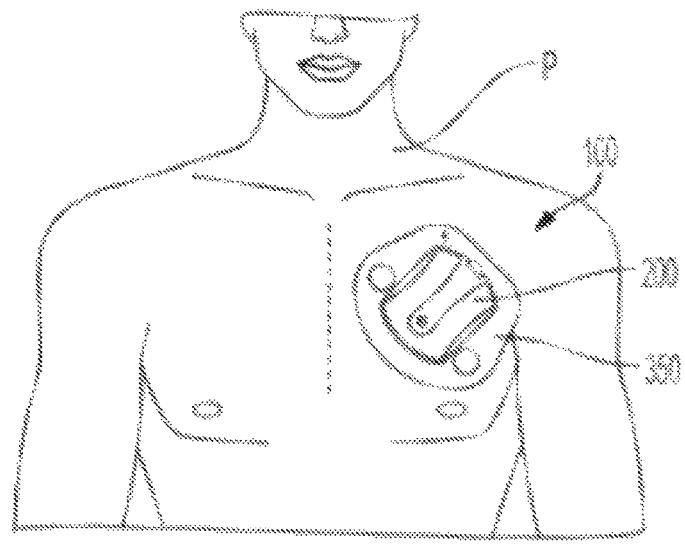
FIG. 2C is a schematic illustration of the patient monitoring system of FIG. 1B worn by the patient in another example configuration of the second possible mode of use.

The multi-mode sensor as described herein can be configured to continuously and/or intermittently acquire physiological data from the patient in at least two modes. For example, in a first mode, the multi-mode sensor can automatically detect that the multi-mode sensor has been removably connected to a holster and associated monitoring cables. Such a configuration would result in the patient monitoring system being configured as shown in FIGS. 1A and 2A below. For example, in a second mode, the multi-mode sensor can automatically detect that the multi-mode sensor has been removably connected to a patch. In an example, the patch can be adhesive attached to the patient's skin at a predetermined location on the patient's torso. Such a configuration would result in the patient monitoring system being configured as shown in FIGS. 1B and 2B-C below. For example, in a third mode, the multi-mode sensor can automatically detect that the multi-mode sensor has been removably connected to a wearable garment. For example, such a wearable garment can include a garment associated with a wearable cardioverter defibrillator (WCD) device such as the LifeVest® from ZOLL Medical Corporation of Chelmsford, MA Such a configuration would result in the patient monitoring system being configured as shown in FIG. 1C below. Other hardware configurations and/or modes are possible and within the scope of this disclosure.

Advantages of these configurations relate to providing caregivers such as clinicians, physicians, cardiologists, emergency attending physicians and other health care practitioners in either an in-patient or out-patient setting with a variety of options, tools, technologies and mechanisms in monitoring patients charged to their care. For example, in one hypothetical scenario, the multi-mode sensor can be packed along with a holster and associated ECG cables and an adhesive patch to be shipped to a cardiologist for use with a patient. The cardiologist can review the patient's medical history, personal preferences, and other factors to determine a configuration (e.g., holster or patch configuration) best suited for the patient. In some examples, the patient's medical history or personal preferences may indicate an intolerance for a long-term adhesive patch with the multi-mode sensor mounted thereon. For instance, the patient may perceive an intolerance for the sensation against the skin from continuous and/or long term wear. The patient may prefer smaller adhesive electrodes that the patient can rotate to various anatomical locations on the upper chest. In another example, the patient may prefer the multi-mode sensor to be mounted within a garment that then monitors the patient via dry ECG sensing electrodes. In some cases, a caregiver may need 2 or 3 standard ECG channel data for a certain patient in their care. The caregiver may take advantage of the option to use the multi-mode sensor in the holster configuration of FIG. 1A and worn in a manner shown in FIG. 2A.

The devices and techniques herein thus afford caregivers flexibility in prescribing an appropriate device for cardiac and/or fluid or other RF monitoring. In some scenarios, a patient may be instructed or may even choose to change between a patch mode or a holster mode as described herein at the patient's home during the monitoring period. For example, if the patient is performing or about to commence a physical activity, the patient may opt to use the device in the patch mode. After completion of the activity, the patient can change to the holster mode in accordance with the patient's personal preferences and comfort.

In certain implementations, the wearable multi-mode sensor(s) as described herein comprise(s) ECG acquisition and processing circuitry that is physically housed within a same enclosure or unit as the radio-frequency (RF) based radar and associated circuitry. In other implementations, the multi-mode sensor(s) comprise(s) only ECG acquisition and processing circuitry and no RF based radar and associated circuitry. In examples where ECG and RF circuitries are disposed within a same physical housing, to overcome potential interferences between the two types of acquisition and processing circuits, in some embodiments, certain steps are taken. Such steps can include, for example, separation of the grounds for the digital circuitry and the RF components, providing shielding for the RF radar components, using different power paths for the ECG processing and other digital circuitry from that of the RF radar components, and further, using filters in the digital circuits to minimize noise effects, implementing ECG filtering to minimize RF high-frequency signals, and designing the circuit layout such that ECG signal paths are physically separated from the RF signal paths.

According to certain embodiments, the wearable multi-mode sensor operates as a monitoring medical device configured to sense one or more predetermined physiologic parameters of a patient; e.g., for remotely monitoring and/or diagnosing a condition of the patient. The wearable device is carried by the patient as he or she goes about their daily routine. Such monitors can be used either patch configuration or mode or holster configuration or mode in mobile cardiac telemetry (MCT) and/or continuous cardiac event monitoring (CEM) applications; e.g., in patient populations reporting irregular cardiac symptoms. Such patients may be prescribed a cardiac monitor for an extended period of time; e.g., days, weeks, months, years. In some mobile cardiac telemetry applications, a portable cardiac monitor can be configured to substantially continuously monitor the patient for a cardiac anomaly, and when such an anomaly is detected, the monitor may automatically send data to a remote server. The remote server may be located within a 24-hour manned monitoring center, where the data is interpreted by qualified, cardiac-trained reviewers and/or caregivers, and feedback provided to the patient and/or a designated caregiver.

According to certain examples, the system further comprises a holster and a patch for housing the sensor(s) and placing the multi-mode sensor(s) in communication with the patient. In addition, the system includes a wireless local communications gateway (GW) for linking the multi-mode sensor(s) to an external or outside server. The server is configured to analyze the continuously transmitted ECG data from the wearable device comprising the multi-mode sensor(s) and includes, for example, databases, automated analysis algorithms, reporting tools, and a web interface (e.g., touchscreen that facilitates interaction between the system and a user such as a patient or health care provider). Various electronic components of the arrhythmia and/or fluid monitoring multi-mode sensor(s), including but not limited to the microcontroller, ECG leads, ECG circuitry, accelerometer (three-axis), RF antenna integrated PCB, RF circuitry, power source (e.g., battery), may be enclosed within reusable, hermetically sealed slender housing made of plastic material (such as a cartridge). According to certain other examples, the multi-mode sensor(s) is/are connected to and in communication with one or more external ECG leads, multi-axis accelerometers, and RF antennas affixed to or associated with a patient's body for acquisition of patient physiological data.

According to certain examples of the present disclosure, one or more wearable medical devices are described in the context of a multi-component patient monitoring system. The wearable devices described herein are configured for long-term and/or extended use or wear by, or attachment or connection to, a patient. For example, devices as described herein may be capable of being used or worn by, or attached or connected to, a patient without substantial interruption; for example, up to 24 hours or beyond (e.g., weeks, months, or even years). In some implementations, such devices may be removed for a period of time before use, wear, attachment, or connection to the patient is resumed; e.g., to change batteries, carry out technical service, update the device software or firmware, and/or to take a shower or engage in other activities, without departing from the scope of the examples described herein.

With reference to FIGS. 1A-4, a patient monitoring system 100 for use in either a patch mode or a holster mode for monitoring physiological data of a patient P is provided in accordance with an example of the present disclosure. The system 100 includes a multi-mode sensor 200 that is configured to continuously and/or intermittently acquire physiological data from the patient P in at least two modes of operation and to transmit the acquired physiological data to a remote location 103 and/or record the acquired physiological data in an internal memory 256. According to an example of the present disclosure, the physiological data acquired by the multi-mode sensor can comprise one or more of patient electrocardiogram (ECG) data, patient posture, patient movement, step count, radio-frequency (RF) based physiological data, body temperature, and/or patient respiration.

In the context of physiological data acquisition by the multi-mode sensor 200, "continuously" also includes uninterrupted collection of sensor data, such as ECG data and/or accelerometer data, with clinical continuity. In this case, short interruptions in data acquisition of up to one second several times an hour or longer interruptions of a few minutes several times a day may be tolerated and can still be seen as "continuous". As to latency in the case of ECG-based arrhythmia monitoring, as a result of such a continuous scheme as described herein, this relates to the overall budget of response time which can amount to between about 5 to about 15 minutes overall response time (e.g., time from when an event onset is detected to when a notification regarding the event is issued). As such, transmission/acquisition latency would therefore be in the order of minutes.

In addition to such continuous monitoring, the multi-mode sensor 200 is also capable of other modes of physiological signal monitoring. For example, the sensor 200 may monitor certain measurements intermittently or on a periodic basis. In some implementations, for RF-based measurements, posture measurements and certain other vital sign measurements, longer interruptions and/or intermittent sampling of several times an hour may be tolerable.

Figure 13:
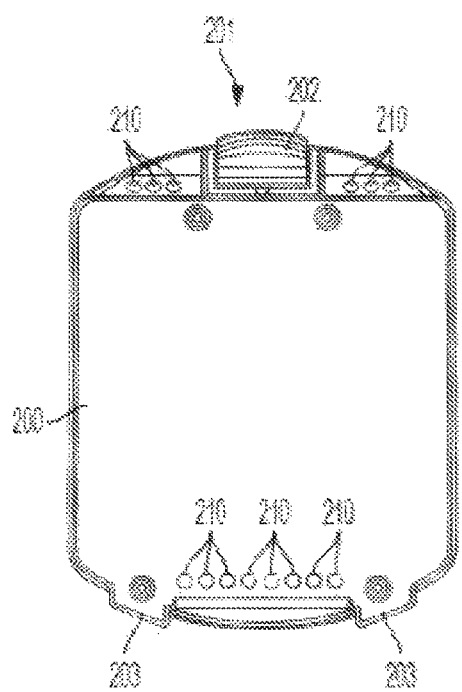
FIG. 13 is a rear view of a multi-mode sensor of the patient monitoring system of FIGS. 1A-1C according to an example of the present disclosure.
Figure 14:
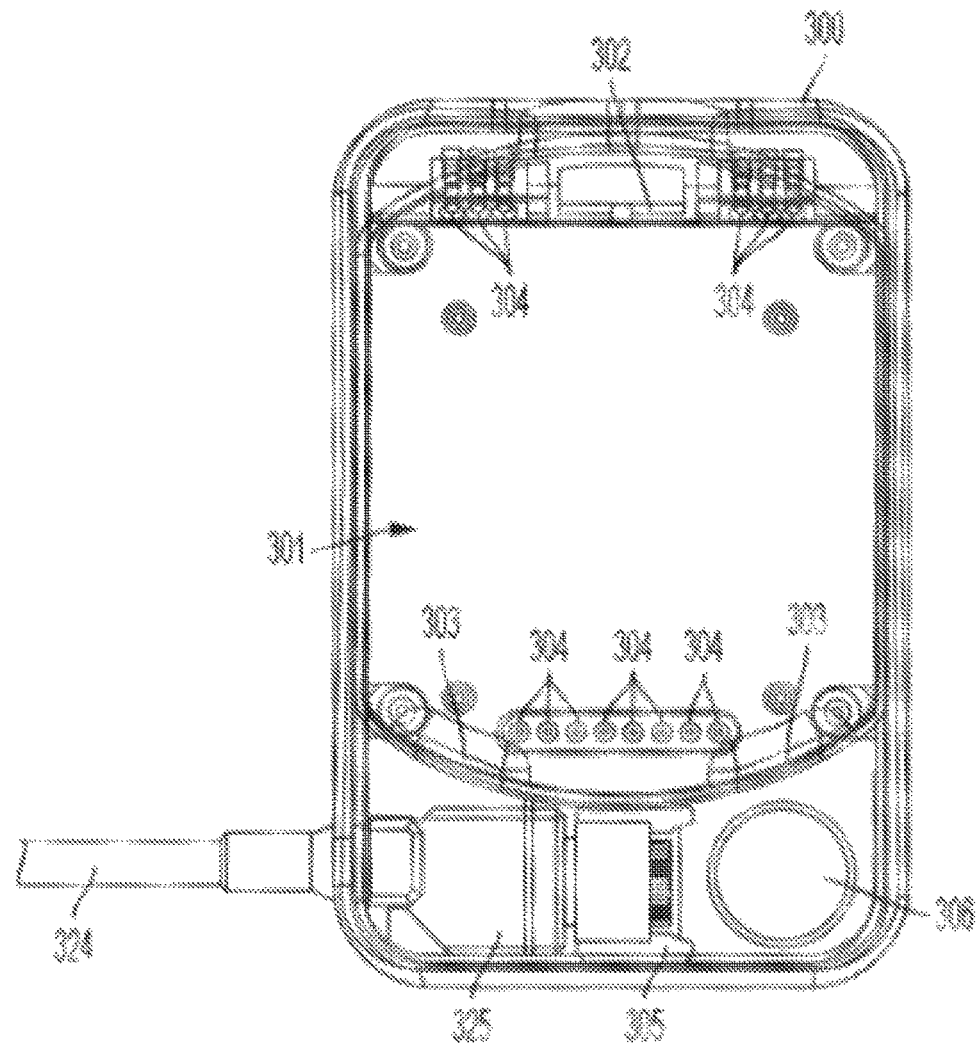
FIG. 14 is a front view of the holster of the patient monitoring system of FIGS. 1A-1C according to an example of the present disclosure.
Figure 15:
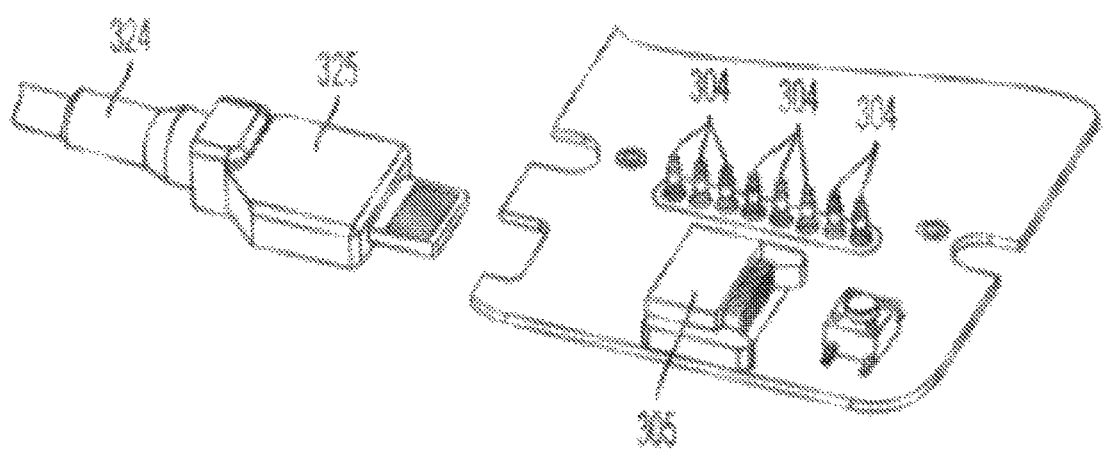
FIG. 15 is a perspective view illustrating connection of a monitoring cable and the holster of FIG. 14.
Figure 16A:
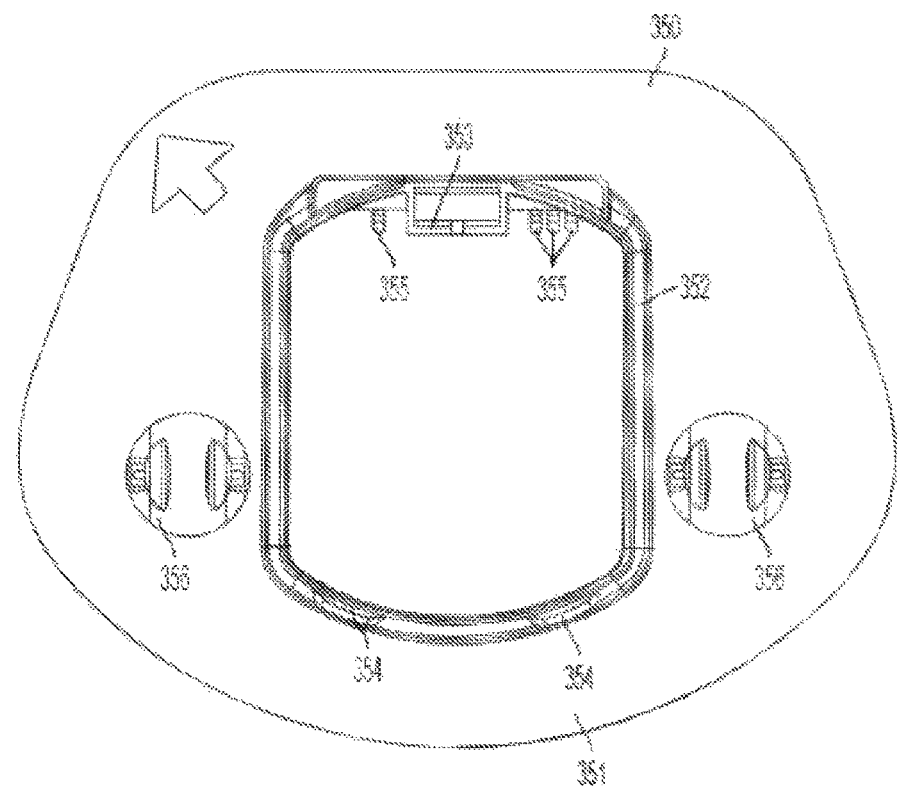
FIG. 16A is a front view of the patch of the patient monitoring system of FIGS. 1A-1C according to an example of the present disclosure.

As shown in FIGS. 1-13, an attachment mechanism 201 is disposed on the multi-mode sensor 200 and is configured to removably connect the multi-mode sensor 200 to at least one of a holster 300 and associated monitoring cables 320 worn by the patient P, a patch 350 worn by the patient P, or an electrode assembly 10 and support garment 20 worn by the patient P. According to certain examples, the attachment mechanism 201 removably connects the multi-mode sensor 200 to both the holster 300 and the patch 350, which incorporate common features that cooperate with the attachment mechanism 201 to connect the multi-mode sensor 200. Alternatively or additionally, the attachment mechanism 201 can also include one or more of the electrical contacts 210 and/or counterpart electrical contacts 304, 355 as described in further detail below. In this manner, the attachment mechanism 201 can perform the function of removably connecting the multi-mode sensor 200 to the holster 300 and/or patch 250 and also establish electrical contact between the sensor 200 and the holster 300 and/or patch 250. As shown in FIG. 13, at least one electrical contact 210 is disposed on the multi-mode sensor 200. The at least one electrical contact 210 is configured to engage a counterpart electrical contact 304 of the holster 300 (shown for example in FIG. 14) and/or a counterpart electrical contact 355 of the patch 350 (shown for example in FIG. 16A). According to certain examples, the at least one electrical contact 210 of the multi-mode sensor 200 comprises a plurality of electrical contacts 210 configured to engage counterpart electrical contacts 304 on the holster 300 and/or counterpart electrical contacts 355 on the patch 350. For example, the contacts 210, 304 can engage the counterpart electrical contacts 305 and 355 through an elastic spring-like tab mechanism such as a POGO pin mechanism. The plurality of electrical contacts 210 on the multi-mode sensor 200 may comprise at least one electrical contact configured to communicate ECG data from the holster 300 and the associated monitoring cables 320 or the patch 350 to the multi-mode sensor 200, at least one electrical contact to communicate accelerometer data from the holster 300 and the associated monitoring cables 320 to the multi-mode sensor 200, and at least one electrical contact configured to transmit power from the multi-mode sensor 200 to the holster 300 and/or from the holster 300 to the multi-mode sensor 200. In implementations including the optional RF circuitry as described herein, the plurality of electrical contacts 210 may also comprise at least one electrical contact configured to transmit an RF signal and/or communicate RF-based physiological data. According to an example of the present disclosure, the at least one electrical contact 210 on the multi-mode sensor comprises a spring-loaded POGO pin. The at least one electrical contact 304 on the holster and/or the at least one electrical contact 355 on the patch 350 may also comprise a POGO pin. It is to be appreciated that the electrical contacts 210, 304, 355 may be of any type or configuration found to be suitable by one having ordinary skill in the art.

With further reference to FIGS. 1A-4, the multi-mode sensor 200 includes configuration circuitry and/or a configuration module 251 disposed therein associated with a microcontroller 250. The configuration circuitry 251 is configured to: determine when the multi-mode sensor is removably connected to the holster 300 and cause the multi-mode sensor 200 to acquire the physiological data in the holster mode when connected to the holster 200, and determine when the multi-mode sensor is removably connected to the patch 350 and cause the multi-mode sensor to acquire the physiological data in the patch mode when connected to the patch 350. The configuration circuitry 251 may also be configured to determine when the multi-mode sensor 200 is removably connected to a garment 20 and to cause the multi-mode sensor 200 to acquire the physiological data in a garment mode when connected to the garment 20.

According to certain examples of the present disclosure, the patient monitoring system 100 is provided with the multi-mode sensor 200 that may be utilized to acquire physiological data from the patient P in a plurality of different modes. According to certain examples of the present disclosure, the types of physiological data acquired by the multi-mode sensor 200 and the manner in which the physiological data is acquired will change depending upon the mode in which the multi-mode sensor 200 is operating and acquiring physiological data. In patch mode, for example, only one channel of ECG acquisition may be powered, operated, and sampled, and/or an internal accelerometer may be powered and operated. In holster mode, at least two channels may be powered, operated, and sampled (e.g., the at least two channels can be sampled using a single ADC by multiplexing the two inputs), and/or the internal accelerometer can be powered down and the external accelerometers can be powered with their data stored together on the device.

In particular, as shown in FIGS. 1A and 2A, the multi-mode sensor 200 is configured to be connected to a holster 300 or a similar holder or receiving device that may be worn by the patient P and/or held by the patient P and/or placed in close proximity to the patient P without being directly adhered to the body or skin of the patient P and to acquire physiological data from the patient P in the holster mode when connected to the holster 300 or similar device. The holster 300 is connected to a plurality of associated monitoring cables 320 having ends placed on the body of the patient P and having one or more devices incorporated therein for acquiring physiological data from the patient P, which is then communicated to the multi-mode sensor 200 via the holster 300, as will be described in further detail below.

As shown in FIGS. 1B, 2B, and 2C, the multi-mode sensor 200 is also configured to be connected to a patch 350 adhered to the skin or body of the patient P by an adhesive and to acquire physiological data from the patient P in the patch mode when connected to the patch 350. One example of a patch 350 suitable for use in connection with the patient monitoring system 100 and the multi-mode sensor 200 is described in United States Patent Application Publication No. 2019/0046038, published on Feb. 14, 2019, the content of which is hereby incorporated by reference in its entirety. The patch 350 is adhered to a skin surface of the body of the patient P, and the patch 350 and/or the multi-mode sensor 200 have one or more devices disposed thereon or incorporated therein for acquiring physiological data from the patient P, which is then communicated to the multi-mode sensor 200, as will be described in further detail below.

As shown in FIG. 1C, the multi-mode sensor 200 may also be configured to be connected to an electrode assembly 10 disposed in or on a support garment 20 worn by the patient P and to acquire the physiological data from the patient in a garment mode when connected to the electrode assembly 10. One example of an electrode assembly 10 and support garment 20 for use in connection with the patient monitoring system 100 and multi-mode sensor 200 is described in United States Patent Application Publication No. 2012/0283794, published on Nov. 8, 2012, the content of which is hereby incorporated by reference in its entirety. The electrode assembly 10 is connected directly or indirectly to the multi-mode sensor 200 and is held in close proximity to the body of the patient P by the support garment 20 such that electrodes 12 can acquire physiological data from the patient P, which is then communicated to the multi-mode sensor 200, as will be described in further detail below.

It is to be appreciated that the example patient monitoring system 100 and multi-mode sensor 200 described herein provide both physicians and patients with a large degree of flexibility in choosing how to use the multi-mode sensor 200 for diagnostic and treatment purposes, how to wear the multi-mode sensor for extended periods of time in the most convenient and/or comfortable manner, and in changing the manner in which the multi-mode sensor 200 is used and worn without requiring replacement of the multi-mode sensor 200 and/or certain other components of the patient monitoring system 100.

For example, with reference to FIGS. 1A and 2A, the holster 300 is configured such that it may be worn on the body of the patient P without being directly attached or affixed to the skin of the patient P. According to one example, the holster 300 may be attached or clipped to a strap or band 309 extending about the waist of the patient P. Other examples of how the patient P may wear the holster 300 will be described in further detail below.

The holster 300 is connected to a plurality of associated monitoring cables 320 having electrode connectors 321 disposed at the distal ends thereof. The electrode connectors 321 are connected to the body of the patient P by respective electrode pads 330, which contain ECG electrodes in contact with the skin of the patient P for sensing ECG signals from the patient P. As shown in FIG. 2A, the patient monitoring system 100 may be provided with three associated monitoring cables 320 and electrode connectors 321 connected to the body of the patient P by the electrode pads 330, which contain the ECG electrodes, at locations on the right anterior of the chest under the right clavicle near the right shoulder within the rib cage frame, on the left anterior of the chest under the left clavicle near the left shoulder within the rib cage frame, and on the lower left of the chest below the pectoral muscles at the lower edge of left rib cage. The example shown in FIG. 2A is a standard configuration and placement for a three-lead ECG placement. Accordingly, when in the holster mode, the multi-mode sensor 200 may acquire ECG data via the associated monitoring cables 320 and the holster 300 in a more standard or traditional multi-channel form, which may be useful to a physician in establishing a baseline for the cardiac activity of the patient P and/or formulating an initial diagnosis of the condition of the patient P. According to other examples of the present disclosure, the multi-mode sensor 200 and the holster 300 may be connected to a five-lead cable assembly 340 (shown in FIG. 21) or a twelve-lead cable assembly.

Further, the associated monitoring cables 320 may each incorporate a 3D accelerometer and associated circuitry 322 (shown in FIGS. 2D and 4) at the distal ends thereof at locations proximate to the electrode pads 330 containing the ECG electrodes, for example within the electrode connectors 321. The 3D accelerometers 322 can thereby be closely associated with the body of the patient P by the electrode connectors 321 and the electrode pads 330 to allow the multi-mode sensor 200 to acquire detailed data concerning the posture, movement, activity, chest motion, and breathing, etc. of the patient P, etc.

Figure 2D:
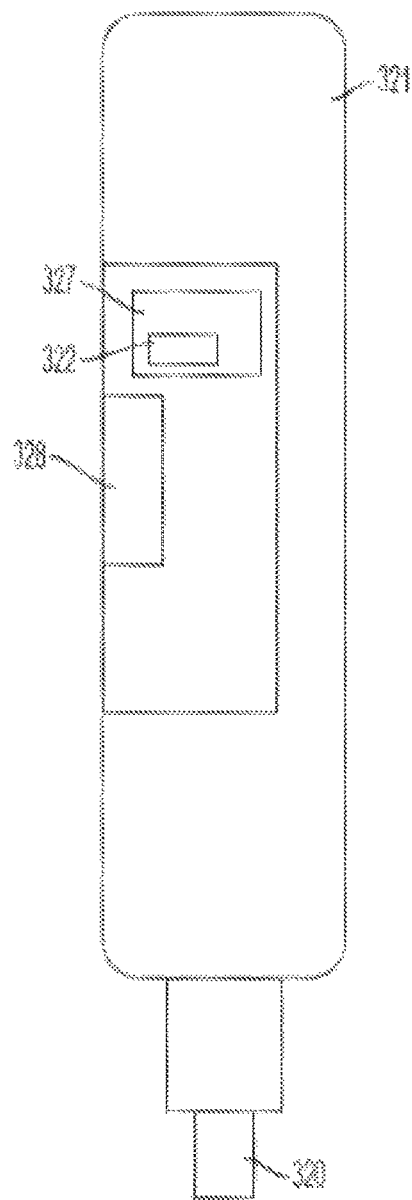
FIG. 2D is a schematic representation of an interior of an electrode connector of the patient monitoring system of FIG. 1A according to an example of the present disclosure.

With reference to FIGS. 1A, 2A, 2D, and 4, in examples, the electrode connectors 321 are disposed in at the distal ends of the cables 320 and couple the cables 320 to the electrode pads 330. As shown in FIG. 2D, the electrode connectors 321 can comprise a circuit 327 (e.g., a printed circuit board or PCB) that includes the 3D accelerometer 322 and a receptacle 328 for receiving a mating connector on the respective electrode pad 330.

The circuit 327 comprises a buffer for either the accelerometer 322 and/or the electrode, thereby tolerating high impedance in the electrode. In examples, the electrode connector 321 can also include a battery (e.g., rechargeable or nonrechargeable) in order to reduce the overall weight of the multi-mode sensor 200 (e.g., by reducing the size/weight of the battery needed in the sensor).

In examples, the 3D accelerometer 322 can also be cardiovibrational sensors for monitoring cardiac electromechanical parameters. For example, such cardiac electromechanical parameters can be useful for diagnosing underlying conditions in heart failure patients. For example, the cardiovibrational signals from such cardiovibrational sensors can be processed by microcontroller 250 to determine one or more cardiovibration metrics. For example, such cardiovibration metrics can include any one or more of electromechanical activation time (EMAT), average EMAT, percentage of EMAT (% EMAT), systolic dysfunction index (SDI), left ventricular systolic time (LVST), S3 sound, and S4 sound. The cardiovibrational sensors can also be configured to detect heart wall motion.

Use of the multi-mode sensor 200 in connection with the holster 300 may be more suitable for the convenience and comfort of the patient P if, for example, the patient P has a negative reaction to the adhesive used in the patch 350 to adhere the patch 350 to the skin of the patient P or is uncomfortable having the patch 350 and multi-mode sensor 200 adhered to his/her skin for an extended period of time. As will be discussed further below, the holster 300 may be worn by the patient P at a variety of different locations on the body of the patient P and may be easily attached to and detached from different articles of the clothing of the patient P.

With reference to FIG. 1C, the multi-mode sensor 200 may be used in connection with a support garment 20 and an electrode assembly 10 carried by the support garment 20. Use of the multi-mode sensor 200 in connection with the support garment 20 and the electrode assembly 10 may be suitable for using the multi-mode sensor 200 in connection with a wearable defibrillator device and electrodes (not shown) also associated with the support garment 20, such as of the type described in United States Patent Application Publication No. 2012/0283794. The patient P may prefer to have a dedicated support garment 20 and electrode assembly 10 for wearing the multi-mode sensor 200 and placing the multi-mode sensor 200 in communication with the body of the patient P. For instance, the electrodes 12 on the electrode assembly 10 are held in contact with the body of the patient P by the support garment 20, thus avoiding the need for the adhesive electrode pads 330 and the adhesive patch 350, which may irritate the skin of the patient P, can require repeated shaving of body hair and the attendant skin irritation for proper adherence to the patient P, and can be painful to remove and replace.

With reference to FIGS. 1B, 2B, and 2C, the patch 350 may be adhered to the skin of the patient P in one of two different configurations, as will be discussed in further detail below. The multi-mode sensor 200 and/or the patch 350 may incorporate one or more radio-frequency (RF) antennas 262, 263 (shown in FIG. 4) for transmitting RF waves into the patient P and receiving reflected RF waves from the patient P in order to acquire RF-based physiological data from the patient P. The patch 350 may also incorporate a pair of ECG electrodes 356 therein for ECG data from the patient P in, for example, a single channel form, which may be useful in determining and diagnosing changes in the cardiac function of the patient P. The multi-mode sensor 200 may also incorporate an internal 3D accelerometer and associated circuitry 258 (shown in FIG. 4) so that additional information concerning the posture, movement, activity, and chest motion and breathing of the patient P can also be acquired by the multi-mode sensor when in the patch mode.

A patient P may prefer using the multi-mode sensor patch 350 for convenience and/or comfort because the patch 350 may have a lighter weight than the holster 300. Also, use of the patch 350 does not require the use of a plurality of cables attached to the patient P, which may restrict movement and can become entangled with the hands and arms of the patient P and restrict the movement of the patient P. Further, the patch 350 is adhered securely to the patient P and is less likely to be inadvertently lost or removed from the patient P.

Table 1 provided below provides a comparison of the patch configuration and/or mode and the holster configuration and/or mode of the multi-mode sensor 200 with respect to the types of physiological data acquired, the functionality of the multi-mode sensor 200, and the components of the system 100 used in connection with the multi-mode sensor according to one example of the present disclosure.

TABLE 1

|  | PATCH MODE | HOLSTER MODE |
|---|---|---|
| ECG | ✓ | ✓ |
| Respiration Rate | ✓ | ✓ For example, based on three accelerometers, can potentially allow detection of respiratory fatigue, shallow breathing, etc. |
| Heart Rate | ✓ | ✓ |
| Posture | ✓ | ✓ For example, multiple accelerometers may allow better assessment of posture, better fall detection, gait measurement may allow fall prediction |
| Activity | ✓ | ✓ For example, multiple accelerometers can provide improved pedometry vs. single accelerometer |
| Patch based | ✓ | ✓ |
| Belt clip option | — | ✓ |
| ECG electrodes | 2 | 3, 5, or 12 |
| Electromagnetic RF generator and a transmitting/receiving antenna | Optional | — |
| Charger | ✓ | ✓ |
| Data transmission device (Gateway) | ✓ | ✓ |
| Server | ✓ | ✓ |

According to one example of the present disclosure, the patient monitoring system 100 may be provided with the multi-mode sensor 200 and the associated components (i.e., the holster 300, associated monitoring cables 320, patch 350, etc.) needed for operating the multi-mode sensor 200 in both the holster mode and the patch mode, as well as possibly the garment mode, so that the physician and the patient P may have the opportunity to choose how best to utilize the patient monitoring system 100 according the physician's needs and preferences with respect to monitoring the condition and cardiac activity of the patient P, establishing a diagnosis(es) of the health condition(s) of the patient P, and the types and nature of the physiological data acquired from the patient P and to choose which configuration of the patient monitoring system 100 best suits the needs of the patient P for convenience and comfort in wearing the multi-mode sensor 200 for an extended period of time (days, weeks, months, years).

Figure 3:
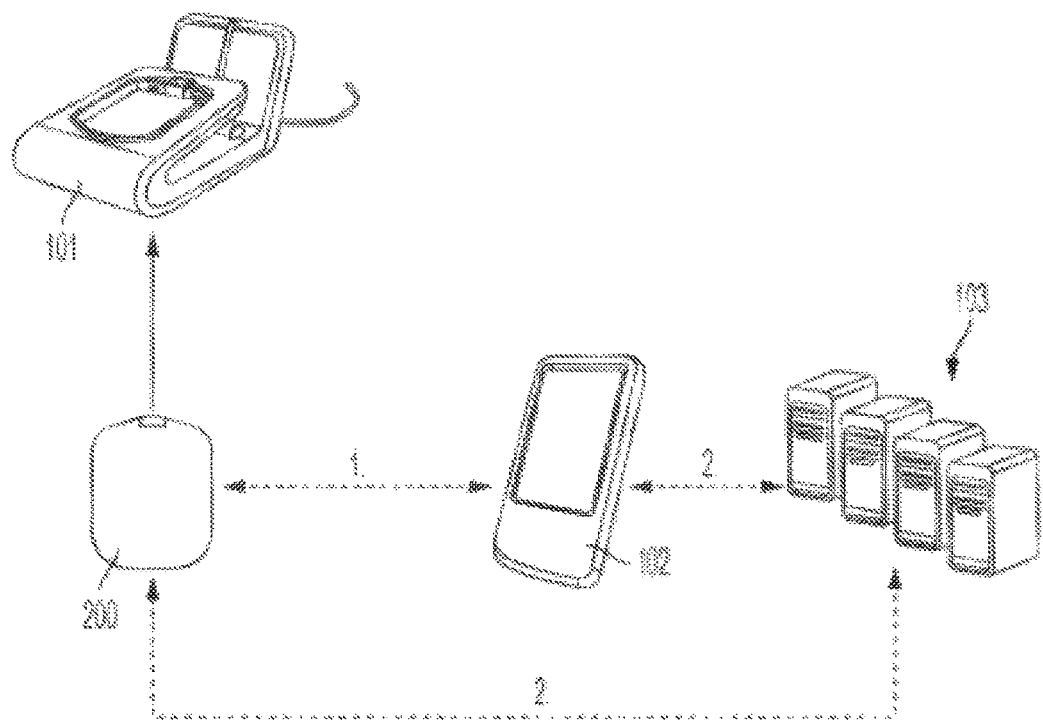
FIG. 3 is a schematic illustration of the transmission of patient physiological data by the patient monitoring system of FIGS. 1A-1C according to an example of the present disclosure.

With reference to FIG. 3, additional components of the patient monitoring system 100 external to the multi-mode sensor 200 are shown in accordance with an example of the present disclosure. As shown, the patient monitoring system 100 includes a charging station 101 for supplying electrical power to the multi-mode sensor 200. Periodically, the multi-mode sensor 200 will need to be disconnected from the holster 300, the patch 350, or the garment 20 and connected to the charging station 101 to re-charge the internal battery 253 (shown in FIG. 4) of the multi-mode sensor 200. The duration and frequency of recharging of the multi-mode sensor 200 may change depending upon the mode in which the multi-mode sensor 200 has been operating. For instance, while operating in the patch mode, the multi-mode sensor 200 may need to be charged for approximately one hour every 5-7 days. While operating in the holster mode, the multi-mode sensor 200 may need to be charged one hour every 2-3 days.

The system 100 also includes the remote location 103, for example a remote server, for receiving transmissions of the physiological data acquired by the multi-purpose sensor 200 for storage of the physiological data, for access to the physiological data by physicians and other authorized medical personnel and/or for re-transmission to physicians and other authorized medical personnel. The system 100 may also include a gateway device 102 or local communications gateway which is configured to receive transmitted data from the multi-mode sensor 200 via a local communications link (1) and to re-transmit the data to the remote location 103 via a longer range communications link (2). According to another example, the multi-mode sensor 200 is configured to communicate directly with the remote location 103 via a longer range communications link (2).

In certain alternative implementations, the holster as described herein can potentially include the gateway device. For example, the holster can include cellular communication capabilities as described herein for the gateway device. In examples, the holster may also serve as a gateway for when the multi-mode sensor is in use in the patch mode. In examples, the holster can include a rechargeable battery to extend battery life for the multi-mode sensor.

In some embodiments, the transmission of data/signals between the multi-mode sensor 200 and the gateway device 102 and/or the remote location 103 may be one-way (e.g., from the multi-mode sensor 200 to the gateway device 102) or the transmission may be bi-directional. Similarly, the transmission of data/signals between the gateway device 102 and the remote location 103 may be one-way (e.g., from the gateway device 102 to the server 103) or bi-directional.

In some embodiments, the multi-mode sensor is configured to monitor, record, and transmit to the gateway device 102 and/or the remote location 103 physiological data about the patient P continuously. In particular, the multi-mode sensor 200 may not interrupt monitoring and/or recording additional data while transmitting already-acquired data to the gateway device 102. In other words, in some embodiments, both the monitoring/recording and the transmission processes occur at the same time or at least nearly at the same time.

As an another example, if the multi-mode sensor 200 does suspend monitoring and/or recording additional data while it is transmitting already-acquired data to the gateway device 102 and/or the remote location 103, the multi-mode sensor 200 may then resume monitoring and/or recording additional data prior to all of the already-acquired data being transmitted to the gateway device 102 and/or the remote location 103. In other words, the interruption period for monitoring and/or recording may be less in comparison to the time it takes to transmit the already-acquired data (e.g., between about 0% to about 80%, about 0% to about 60%, about 0% to about 40%, about 0% to about 20%, about 0% to about 10%, about 0% to about 5%, including values and subranges therebetween), facilitating the near-continuous monitoring and/or recording of additional data during transmission of already-acquired physiological data. For example in one specific scenario, when a measurement time duration is around 2 minutes, any period of suspension or interruption in the monitoring and/or recording of subsequent measurement data may range from a just few milliseconds to about a minute. Example reasons for such suspension or interruption of data may include allowing for the completion of certain data integrity and/or other on-line tests of previously acquired data as described in further detail below. If the previous measurement data has problems, the multi-mode sensor can notify the patient P and/or remote technician of the problems so that appropriate adjustments can be made.

In some embodiments, the bandwidth of the link between the multi-mode sensor 200 and the gateway device 102 may be larger, and in some instances significantly larger, than the bandwidth of the acquired data to be transmitted via the link (e.g., burst transmission). Such embodiments ameliorate issues that may arise during link interruptions, periods of reduced/absent reception, etc. In some embodiments, when transmission is resumed after interruption, the resumption may be in the form of last-in-first-out (LIFO). The gateway device 102 can be configured to operate in a store-and-forward mode where the data received from the multi-mode sensor 200 is first stored in an onboard memory of the gateway device 102 and then forwarded to the remote location 103. For example, such a mode can be useful where the link with the remote location 103 may be temporarily unavailable. In some embodiments, the gateway device 102 can function as a pipe line and pass through data from the multi-mode sensor immediately to the remote location 103. In further examples, the data from the multi-mode sensor may be compressed using data compression techniques to reduce memory requirements as well as transmission times and power consumptions.

In some embodiments, the multi-mode sensor 200 may be configured to monitor, record, and transmit some data in a continuous or near-continuous manner as discussed above, while monitoring, recording, and transmitting some other data in a non-continuous manner (e.g., periodically, no-periodically, etc.). For example, the multi-mode sensor 200 may be configured to record and transmit electrocardiogram (ECG) data continuously or nearly continuously while radio-frequency (RF) based measurements and/or transmissions may be periodic. For example, ECG data may be transmitted to the gateway device 102 (and subsequently the remote location 103) continuously or near-continuously as additional ECG data is being recorded, while RF-based measurements may be transmitted once the measuring process is completed.

Monitoring and/or recording of physiological data by the multi-mode sensor 200 may be periodic, and in some embodiments, may be accomplished as scheduled (i.e., periodically) without delay or latency during the transmission of already-acquired data to the gateway device 102. For example, the multi-mode sensor 200 may acquire physiological data from the patient P in a periodic manner and transmit the data to the gateway device 102 in a continuous manner as described above.

As discussed above, the multi-mode sensor 200 may be configured to transmit the acquired data to the remote location 103 instead of, or in addition to, transmitting the data to the gateway device 102. The multi-mode sensor 200 may also be configured to store some or all of the acquired physiological data in the memory 256. In some embodiments, the transmission of data from the multi-mode sensor 200 to the gateway device 102 may be accomplished wirelessly (e.g., Bluetooth®, etc.) and/or via a wired connection. The transmission of data from the gateway device 102 to the remote location 103 may also be accomplished wirelessly (e.g., Bluetooth®-to-TCP/IP access point communication, Wi-Fi®, cellular, etc.) and/or via a wired connection.

As mentioned above, in some embodiments, the transmission of data and/or signals occurs via two links, the links between the multi-mode sensor 200 and the gateway device 102 (e.g., Bluetooth® link) and between the gateway device 102 and the remote location 103 (e.g., Wi-Fi®, cellular). The Bluetooth® link can be a connection bus for multi-mode sensor 200 and remote location 103 communication, used for passing commands, information on status of the microcontroller 250 of the multi-mode sensor 200, measurement data, etc. In some embodiments, the microcontroller 250 of the multi-mode sensor 200 may initiate communication with the remote location 103 (and/or the gateway device 102), and once connection is established, the remote location 103 may be configured to initiate some or all other communications. In some embodiments, the gateway device 102 may be configured to conserve the power available to the multi-mode sensor 200, gateway device 102, and/or the remote location 103. For example, one or both links may enter power-saving mode (e.g., sleep mode, off-state, etc.) when the connections between the respective devices/location are not available. As another example, the transmission of data may also be at least temporarily interrupted when the link quality (e.g., available bandwidth) is insufficient for at least a satisfactory transmission of the data. In such embodiments, the gateway device 102 may serve as a master device in its relationship to one or both of the multi-mode sensor 200 and the remote location 103.

In some embodiments, the gateway device 102 may be considered as a simple pipe, and/or the sensor-gateway device-server path may be defined as a single link; i.e., the link performance may depend on the bottleneck between the sensor-gateway device and gateway device-server links. In some embodiments, at least the main bottleneck may be the gateway device-server link, since the gateway device 102 is carried by the patient in close proximity to the device, while the gateway device-server link (e.g., cellular or Wi-Fi® coverage) is expected to be variable. In some embodiments, a "best effort delivery" quality-of-service may be sufficient for the Bluetooth® link and/or the TCP/IP link, since the transmitted data is processed (with some latency, for example) and is used for displaying notifications (for example, instead of being presented online to a monitoring center). In some embodiments, a single gateway device 102 may be configured to serve a plurality of sensors; i.e., the plurality of sensors may be connected to a single gateway device 102 via respective links. In some embodiments, there may be a plurality of gateway devices 102 serving one or more sensors 200; i.e., each sensor 200 of one or more sensors 200 may be connected to a plurality of gateway devices 102 via respective links.

In some embodiments, the transmission links may be configured to withstand co-existence interference from similar devices in the vicinity and from other devices using the same RF band (e.g., Bluetooth®, Cellular, Wi-Fi®). Standard Bluetooth® protocol and/or standard TCP/IP protocols, as well as the addition of cyclic redundancy checks to the transmitted data, may be used to address any issue of interference. Further, to preserve the security of wireless signals and data, in some embodiments, data transfer between the sensor and the server may be done using a proprietary protocol. For example, TCP/IP link may use SSL protocol to maintain security, and the Bluetooth® link may be encrypted. As another example, UDP/HTTP may also be used for secure transmission of data. In some embodiments, only raw binary data may be sent, without any patient identification. In implementations, the sensor may be configured to detect changes in arrhythmia and send ECG strips only around the onset and offset of such arrhythmia events. In some examples, the sensor may be configured to store the data for several days (e.g., 7 days, 14 days, 30 days, 45 days, 90 days, or other configurable period of time depending on memory storage capacity) and transmit the data only at the end of use or upon return to the factory (e.g., for holster applications).

Figure 4:
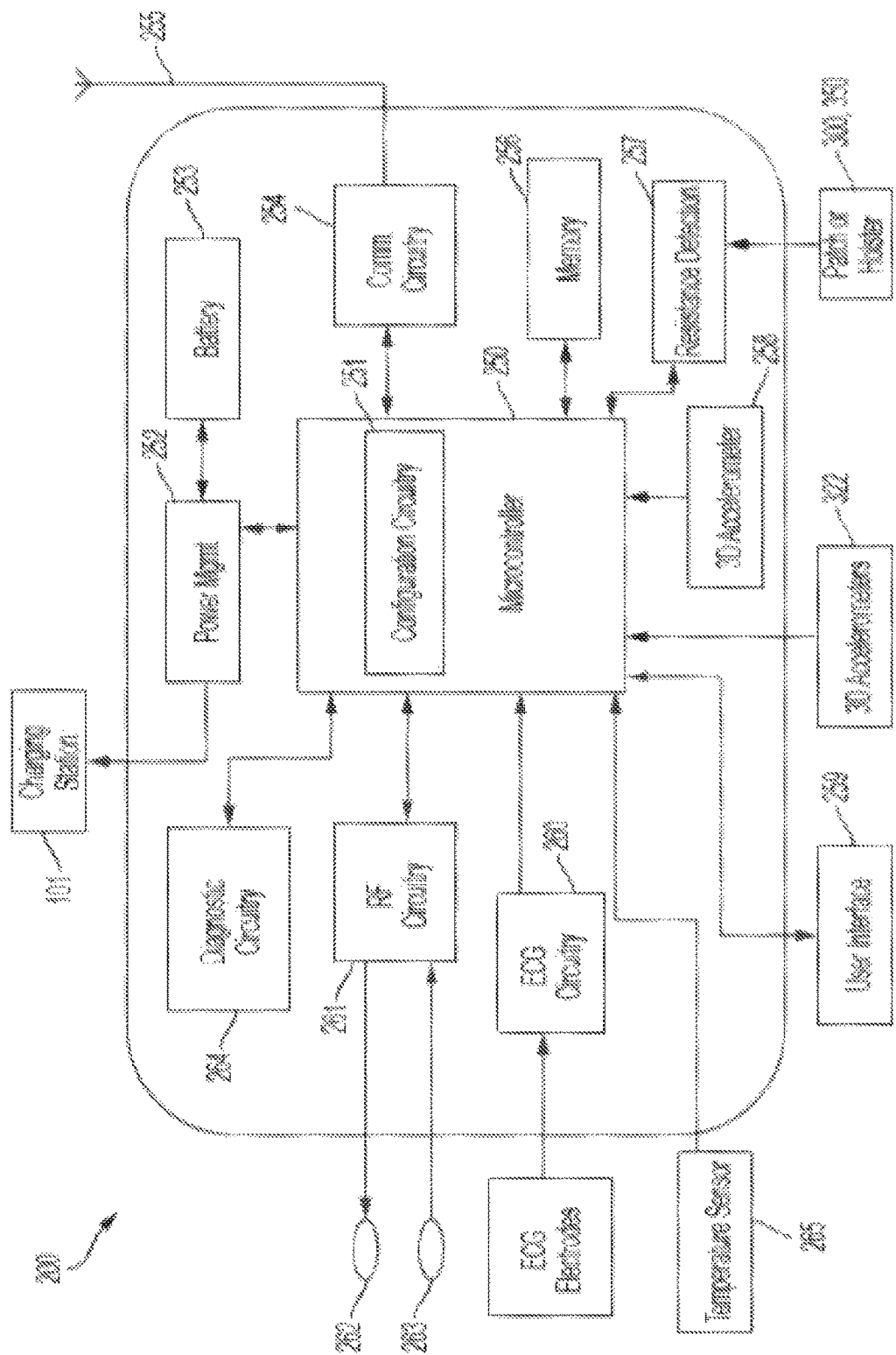
FIG. 4 is a schematic illustration of device electronics architecture for measurement and transmission of patient physiological data by the patient monitoring system of FIGS. 1A-1C according to an example of the present disclosure.
Figure 5:
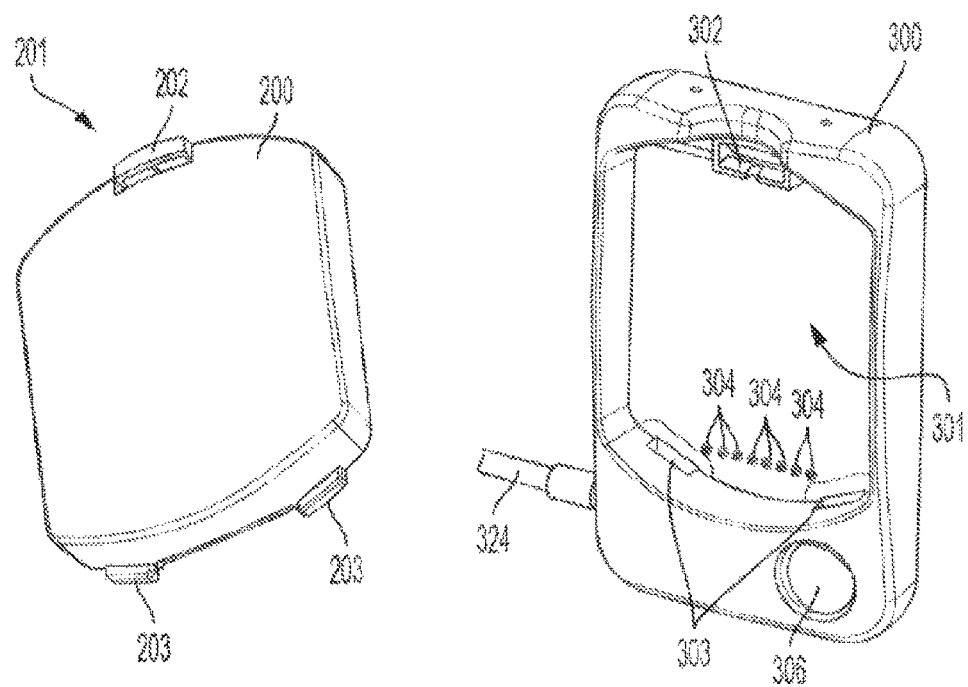
FIG. 5 is an exploded perspective view of a multi-mode sensor and holster of the patient monitoring system of FIGS. 1A-1C according to an example of the present disclosure.

With reference to FIG. 4, the internal components of the multi-mode sensor 200 are shown in accordance with an example of the present disclosure. As shown, the multi-mode sensor 200 includes the microcontroller 250, in particular a suitable micro-processor device, in communication with a memory 256 configured to store the software instructions executed by the microcontroller 250 for performing the various operations of the multi-mode sensor 200 and, in some examples, the physiological data of the patient P acquired by the multi-mode sensor 200 for subsequent communications to the remote location 103 or for reading off of the multi-mode sensor 200 via a physical data link.

The multi-mode sensor 200 includes power management circuitry or a power management module 252 and a battery 253 for providing electrical power to the multi-mode sensor 200. The power management module 252 is configured to communicate the microcontroller 250/configuration circuitry 251 and the battery 253 with the charging station 101. The configuration circuitry 251 is configured to determine when the multi-mode sensor 200 is removably connected to the charging station 101 or other charger device and cause the battery 253 to be charged.

The multi-mode sensor 200 includes communications circuitry or a communications module 254 and at least one communications antenna 255 for transmitting to and receiving signals and information from the remote location 103 and/or the local communications gateway 102. According to one example, the communications circuitry 254 is configured to transmit the acquired physiological data to the remote location 103 via the local communications gateway 102 through a local communications link (1) (e.g., Bluetooth®, Wi-Fi®, Zigbee®, etc.). According to another example, the communications circuitry 254 is configured to transmit the acquired physiological data to the remote location 103 directly via a longer-range communications link (2), such as a cellular telecommunications signal.

According to certain examples of the present disclosure, the patient monitoring system 100 may comprise one or more user interfaces 259 disposed on or associated with the multi-mode sensor 200. The user interfaces 259 may be provided to allow the patient P and/or the physician or other medical personnel to interact with and provide commands to the multi-mode sensor 200 and/or the holster 300, to view or observe the operational status of the multi-mode sensor 200 or other components of the system 100, to receive signals and feedback (visual, audible, tactile) from the multi-mode sensor 200, and to receive indications or readouts regarding the physiological data acquired by the multi-mode sensor. According to one example illustrated in FIGS. 5, 7, and 14, the user interface may be a symptom report button 306 on the holster 300 actuated by the patient P to generate an event report at a time when the button 306 is actuated, as will be discussed in further detail below.

It is to be appreciated that system 100 may be provided with additional or alternative user interfaces 259 found to be suitable to those having ordinary skill in the art. For instance, the user interfaces 259 may comprise buzzers, vibrators, or alarms for alerting the patient P that the multi-mode sensor 200 has detected an arrhythmia event, or that the multi-mode sensor 200 is low on power or has become disconnected from the holster 300, the monitoring cables 320, or the patch 350. The user interfaces 259 may comprise LCD or LED screens visually indicating the operational status of the multi-mode sensor and/or the acquired physiological data. The user interfaces 259 may comprise one or more touch screens, buttons, keys, knobs, or switches for inputting information and commands to the multi-mode sensor 200. The user interface 259 may also comprise a button for initiating an emergency telephone call or alert to the physician, a designated caregiver, emergency medical personnel, hospital or care facility staff, or 911 service. The holster 300 may also be provided with an accelerometer or similar device so that a patient input to the holster 300 and/or the multi-mode sensor 200 can be made by tapping (i.e., a double tap) on the holster 300. The multi-mode sensor 200 may also be configured to recognize such tapping commands through the accelerometers 258, 322 discussed below.

According to an example of the present disclosure, a resistance level provided in a connection between the at least one electrical contact 210 of the multi-mode sensor 200 and the at least one electrical contact 304 of the holster 300 is different from a resistance level provided in a connection between the at least one electrical contact 210 of the multi-mode sensor 200 and the at least one electrical contact 355 of the patch 350. The multi-mode sensor 200 may include resistance detection circuitry or a resistance detection module 257 configured to detect the resistance level between the at least one electrical contact 210 of the multi-mode sensor 200 and the counterpart electrical contact 304 of the holster 300 or the counterpart electrical contact 355 of the patch 350. The configuration circuitry 251 is configured to determine when the multi-mode sensor 200 is removably connected to the holster 300 or the patch 350 (or possibly the garment 20) based on the detected resistance level. It is to be appreciated that detecting resistance levels is one way that the configuration circuitry 251 of the multi-mode sensor 200 can determine when the multi-mode sensor 200 is connected to the holster 300 or the patch 350 and that any means or mechanism found to be suitable by one having ordinary skill in the art for making this determination may be used in connection with the multi-mode sensor 200.

According to an example of the present disclosure, the multi-mode sensor 200 is configured to detect a disconnect between the holster 300 and the monitoring cables 320 and/or between the monitoring cables 320 and the patient P when in the holster mode. For instance, a high electrical impedance in the signal carrying ECG data to the multi-mode sensor 200 will be generated when a disconnect occurs between the monitoring cables 320 and the patient P and/or between the monitoring cables 320 and the holster 300. The multi-mode sensor 200 may be configured to detect the increased impedance or the interruption or loss of the ECG signal from the ECG electrodes. The multi-mode sensor 200 may be configured to generate an audible, visual, or tactile alarm or indicator via a user interface 259, as discussed above, to indicate to the patient P that such a disconnect has occurred.

The physiological data acquired by the multi-mode sensor 200 may comprise accelerometer data that can be interpreted by the multi-mode sensor 200 and/or software operating at the remote location 103 to indicate patient posture, patient movement and activity, and/or patient respiration and respiration rate. The multi-mode sensor 200 includes a 3D (multi-axis) accelerometer 258 and associated circuitry and is configured to monitor for at least one of: patient posture, patient movement, and/or patient respiration based on the accelerometer data from the 3D accelerometer 258. The 3D accelerometer 258 may be used to generate accelerometer data in both the patch mode and the holster mode. The multi-mode sensor 200 is also configured to receive accelerometer data from 3D (multi-axis) accelerometers 322 provided on the distal ends of the monitoring cables 320 and to monitor for at least one of: patient posture, patient movement, and/or patient respiration based on the accelerometer data from the 3D accelerometers 322 when in the holster mode. The multi-mode sensor 200 is configured to transmit the accelerometer data to the remote location 103 via the communications circuitry 254. The accelerometer data may also be used in conjunction with acquired ECG data and RF-based physiological data to assess lung or thoracic fluid levels or to aid RF and/or ECG analysis by detecting different types of motion segments in the recording so that the conditions of the measurements of the RF and/or the ECG may be interpreted/analyzed accordingly. For example, in some embodiments, RF and/or ECG measurements may be performed while the patient wearing the sensor is active or at rest. The analysis of the RF and/or ECG data may then depend on the state of the physical activity of the patient P (e.g., at rest, low-intensity activity, high-intensity activity, etc.). In such embodiments, the accelerator may be used to identify the physical state of the patient P so as to properly analyze and interpret the RF and/or ECG measurements.

The accelerometer data may also be utilized to assess other patient conditions, such as sleep apnea, respiratory fatigue, and rapid shallow breathing, or to determine if the patient P has experienced a fall. The accelerometer data, in some implementations, can be used to monitor for changes in gait (in a hypothetical scenario, after establishing a baseline gait, monitor for deviations over a predetermined prescriber-controlled threshold, such as 20% or more, from the baseline gait). Such change in gait can indicate a precursor to a fall event (e.g., the patient is about to fall). The multi-mode sensor 200 may be configured to generate a signal to the physician, a dedicated caregiver, hospital or care facility staff, emergency medical personnel, or a 911 service if a patient fall has been detected. Other details and benefits with respect to providing the 3D accelerometers 258, 322 in connection with the multi-mode sensor are discussed in the above-mentioned United States Patent Application Publication No. 2019/0046038.

According to an example, the accelerometer data generated by the 3D accelerometers 258, 322 may be used to determine if the ECG electrodes and/or the monitoring cables 320 have been applied to the patient P correctly during walking, sleeping, and/or sitting. The multi-mode sensor 250 may establish a baseline accelerometer signal for each of the accelerometers 258, 322 during walking, lying down, and sitting. For example, such a baseline can be based on the patient interacting with a user interface element 259 to indicate what type of activity (walking, sleeping, sitting, etc.) the patient is performing. Once the activity is established, the ACC signal is stored corresponding to the activity. This baseline is used to compare to ACC signals during regular use to determine if the electrodes were correctly applied.

The accelerometers 322 may also be configured to identify the ECG electrodes to the multi-mode sensor 200 by tapping on the distal ends of the monitoring cables 320 containing both the electrode connectors 321 and the accelerometers 322. Alternatively or additionally, the accelerometers 322 can be configured to detect movement when applying the electrode onto the body. The accelerometers 322 may also be used to detect movement of the ECG electrodes on the body of the patient P or removal of the ECG electrodes from the patient P.

The physiological data acquired by the multi-mode sensor 200 may comprise ECG data. The multi-mode sensor 200 includes ECG circuitry or an ECG module 260 in communication with the ECG electrodes contained in the electrode pads 330 connected to the monitoring cables 320 or the ECG electrodes 356 disposed in or on the patch 350. The ECG circuitry 260 is configured to communicate with at least one ECG channel formed by the ECG electrodes and continuously acquire ECG data from the patient P. In particular, when in the patch mode, the ECG circuitry 260 is configured to acquire the ECG data from the patient P via at least one ECG channel formed by the ECG electrodes 356 on the patch. When in the holster mode, the ECG circuitry 260 is configured to acquire the ECG data from the patient via at least two ECG channels formed by the ECG electrodes connected to the monitoring cables 320. The multi-mode sensor 200 is configured to transmit the ECG data based on the one or more ECG channels to the remote location 103 via the communications circuitry 254 and antenna 255.

In implementations where RF circuitry is included, the physiological data acquired by the multi-mode sensor 200 may comprise RF-based physiological data (e.g., lung fluid level/content, thoracic fluid level/content, heart wall movement, arterial pulse motion, etc.). The multi-mode sensor 200 further includes at least one radio-frequency (RF) antenna 262, 263 disposed on a patient-facing side, i.e., the rear side shown in FIG. 13, of the multi-mode sensor 200. Alternatively, the at least one RF antenna 262, 263 may be stitched into the material of the patch 350 on the patient-facing side. The at least one antenna 262, 263 is configured to transmit RF waves from the multi-mode sensor 200 into the patient P and to receive reflected RF waves from the patient P. In particular, the multi-mode sensor 200 includes a RF transmitter antenna 262 for transmitting the RF waves and a RF receiver antenna 263 for receiving the reflected RF waves from the patient P. The multi-mode sensor 200 also comprises RF circuitry or a RF module 261 configured to acquire the RF-based physiological data from the patient P when in the patch mode. Further details regarding the RF components of the multi-mode sensor 200, the capabilities and operation of the multi-mode sensor 200 with respect to acquiring the RF-based physiological data, and the purposes and interpretation of the RF-based physiological data with respect to patient diagnosis and monitoring are discussed in the above-mentioned United States Patent Application Publication No. 2019/0046038. The multi-mode sensor 200 is configured to transmit the RF-based physiological data to the remote location 103 via the communications circuitry 254.

The RF antennas 262, 263 are configured to direct electromagnetic waves into the body of the patient P and receive waves that are scattered and/or reflected from internal tissues. The RF circuitry 261 is configured to process the received waves so as to determine some properties of the tissues that are on the path of the transmitted and/or scattered/reflected waves. For example, the antennas 262, 263 may direct RF waves toward a lung of a patient, and the RF circuitry 261 may analyze the scattered/reflected waves to perform an RF-based measurement of the lung fluid level of the patient.

The physiological data acquired by the multi-mode sensor 200 may comprise body temperature of the patient P. The multi-mode sensor 200 may comprise a temperature sensor 265 disposed on or external to the multi-mode sensor 200 that is configured to sense the body temperature of the patient P. According to one example, the temperature sensor 265 is provided at the distal end of at least one of the monitoring cables 320. The temperature sensor 265 may also be provided in or on the patch 350. The multi-mode sensor 200 is configured to transmit the temperature data to the remote location 103 via the communications circuitry 254.

In some embodiments, the multi-mode sensor 200 may also include a conductance sensor, a pressure sensor, a respiration sensor, SPO2, and/or a light sensor. For example, a respiration sensor can include an accelerometer configured to monitor the chest movements of the patient P, e.g., during certain portions of the day and/or night or during an RF measurement. For instance, a 3D multi-axis, multi-channel accelerometer, for instance one or more of the accelerometers 258, 322 discussed above or in addition thereto, can be configured to, on a first channel, monitor for a patient movement and/or posture, and on a second, different channel, monitor the chest movements of the patient to determine respiration rate and other related data. Alternatively, a respiration accelerometer can be provided in the device that is separate from a posture-sensing accelerometer. In some examples, the respiration rate measurement can be based on the operation of a tri-axis micro-electromechanical system (MEMS) accelerometer within the device mounted on the torso of the patient P. The accelerometer can measure projections of the gravity vector on its intrinsic axes. From these measurements, a respiration rate can be derived based on measured quasi-periodic changes of the projections that occur due to respiration movements of the rib cage of the patient P.

In other examples, the respiration rate and/or other respiration data can be derived from the RF signals themselves. For example, dedicated respiration circuitry can be provided and/or the microcontroller 250 can be configured with instructions to cause the microcontroller 250 to monitor the reflected RF waves as described herein and determine respiration rate and related data therefrom.

In some embodiments, respiration characteristics such as exhale vs. inhale times can also be measured via an accelerometer. One or more accelerometers, such as the accelerometers 258, 322 discussed above, may be applied to the chest and at the lower part of the rib cage (e.g., close to the diaphragm) of the patient. Health conditions such as sleep apnea, respiratory fatigue, and rapid shallow breathing may be detected by the multi-mode sensor 200 from the accelerometer measurements from such accelerometers 258, 322.

In some embodiments, RR, which denotes ventricular interbeat interval on ECG, may be derived from ECG data, and the RR accuracy can be improved by fusing the data from two or more of these RR measurement methods. In some embodiments, the multi-mode sensor 200 is also configured to obtain a photoplethysmogram (PPG) via a light sensor.

According to an example of the present disclosure, the multi-mode sensor 200 comprises diagnostic circuitry or a diagnostic module 264 configured to detect a physiological condition of the patient P based on the acquired physiological data. For instance, the diagnostic circuitry 264 may be configured to interpret/use the patient ECG data acquired by the multi-mode sensor 200 to detect certain physiological conditions of the patient, such as a cardiac arrhythmia (e.g., atrial fibrillation, bradycardia, tachycardia, asystole, heart pauses, and/or erratic heart rates).

With reference to FIGS. 1A, 2A, 2D, 5-7, 13-15, and 17-21, the patient monitoring system 100 includes the holster 300 configured to removably receive the multi-mode sensor 200 and the associated monitoring cables 320. The holster 300 includes a recessed area or receiver 301 receiving the multi-mode sensor 200 therein. The receiver 301 includes features configured to be engaged by the attachment mechanism 201 of the multi-mode sensor 200, as will be discussed in further detail below. The receiver 301 of the holster 300 also includes one or more electrical contacts 304 that can be engaged by corresponding electrical contacts 210 on the multi-mode sensor 200 for placing the multi-mode sensor 200 in communication with the holster 300 and the associated monitoring cables 320.

The associated monitoring cables 320 comprise a plurality of separate cables 320 comprising distal and opposing ends. The system 100 also comprises a plurality of ECG electrodes corresponding to the plurality of separate cables 320. Each of the ECG electrodes is connected to a distal end of a corresponding cable 320 and is configured to be releasably attached to the skin of the patient P. For example, each ECG electrode may be located in a respective electrode pad 330 secured to the skin of the patient P by an adhesive. Each cable 320 may include an electrode connector 321 defining a receptacle 328 for receiving a mating connector on the respective electrode pad 330. The electrode connector 321 may also include a circuit 327 including one or more sensing or electrical components of the electrode connector 321.

The associated monitoring cables 320 may be provided as part of a cable assembly. According to an example, the assembly may include a connector 323. The opposing ends of the plurality of separate cables 320 may be mechanically coupled to the connector 323. The cable assembly may also include a main monitoring cable 324 comprising a connector end coupled to the connector 323 and a holster end configured to be releasably or non-releasably connected to the holster 300. In particular, the holster end of the main monitoring cable 324 may comprise a cable connector 325. The holster 300 may comprise a cable receiver 305, e.g., a card-edge connector, configured to releasably receive cable connector 325 at the holster end of the main monitoring cable 324. The cable connector 325 and the cable receiver 305 may each include one or more complementary electrical contacts to allow for data to be transmitted from the monitoring cables 320 to the holster 300 and the multi-mode sensor 200. According to an example, the assembly of the monitoring cables 320, connector 323, main monitoring cable 324, and cable connector 325 is made from a disposable, recyclable material and does not include any batteries or potted electrical materials. In examples, the entire assembly can be constructed as a one-piece cable/holster assembly that is disposable and/or recyclable.

With reference to FIGS. 1A and 2A, according to certain examples of the present disclosure, the plurality of ECG electrodes on the associated cables 320 may comprise at least two, more particularly three, ECG electrodes, which are attached to the skin of the patient P. The ECG electrodes are configured to detect the ECG signals of the patient P. The system 100 may be configured to provide at least one, more particularly three, ECG channels based on the at least two, more particularly three, ECG electrodes provided on the associated cables 320. As discussed above, the three ECG electrodes may be arranged on the body of the patient P at locations on the right anterior of the chest under the right clavicle near the right shoulder within the rib cage frame, on the left anterior of the chest under the left clavicle near the left shoulder within the rib cage frame, and on the lower left of the chest below the pectoral muscles at the lower edge of left rib cage. The arrangement of the ECG electrodes on the patient P shown in FIG. 2A is a standard arrangement to provide three ECG channels for obtaining ECG data from the patient P. It is to be appreciated that the ECG electrodes may be arranged on the patient P in any manner found to be suitable for those having ordinary skill in the art for obtaining ECG data from the patient.

Figure 21:
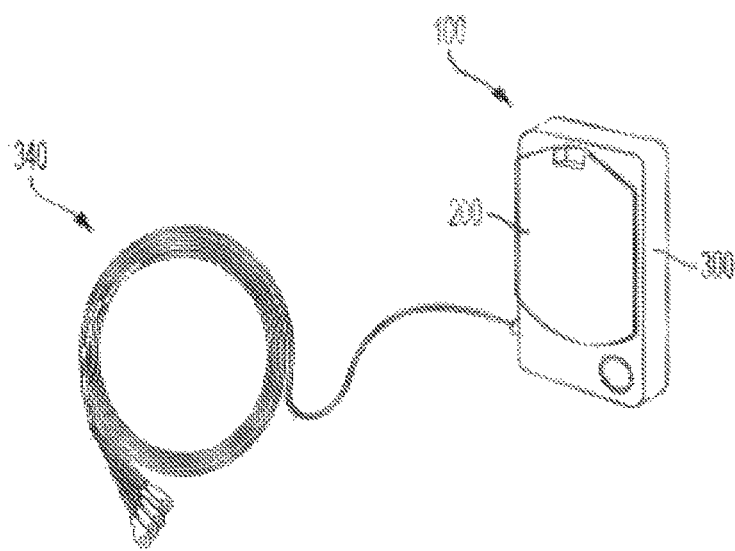
FIG. 21 is a perspective view a patient monitoring system in the first possible mode of use according to another example of the present disclosure.

With reference to FIG. 21, according to an alternative example of the present disclosure, the patient monitoring system 100 comprises a five-cable assembly 340 having five ECG electrodes at the distal ends of the respective cables for attachment to the skin of the patient P. It is to be appreciated that the multi-mode sensor 200 and the holster 300 may be used in connection with any configuration monitoring cables, number of electrodes, and manner of obtaining ECG data found to be suitable to those having ordinary skill in the art. For instance, the multi-mode sensor 200 and the holster 300 may be used in connection with a 12 ECG lead cable assembly.

With reference to FIGS. 2D and 4, each of the distal ends of the plurality of separate cables 320 may also comprise a 3D accelerometer and associated circuitry 322. According to one example, the 3D accelerometer 322 is incorporated in the circuit 327 provided in the electrode connector 321. The multi-mode sensor 200 is configured to monitor for at least one of: patient posture, step count, patient movement, and/or patient respiration, based on the accelerometer data provided by the 3D accelerometers 322, as discussed above.

Figure 6:
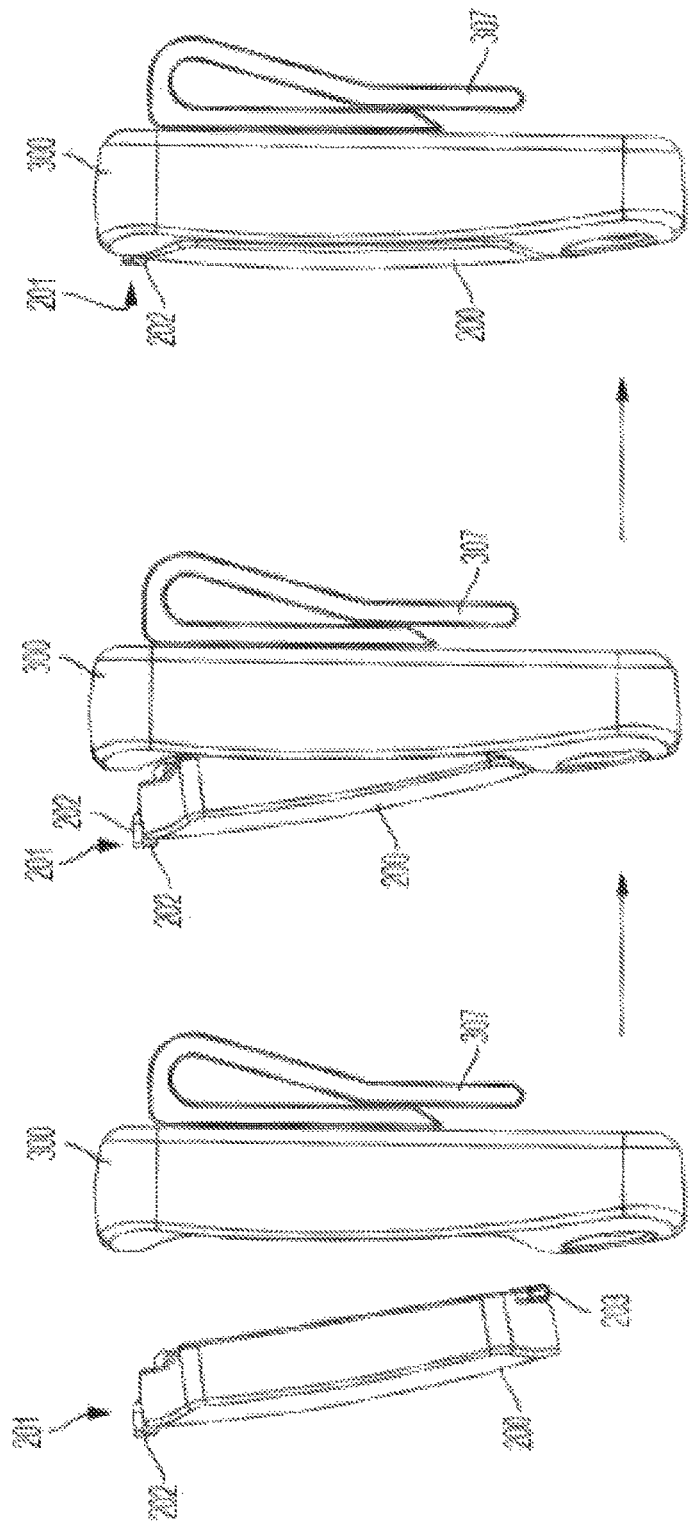
FIG. 6 is a sequential illustration of side views of the multi-mode sensor and holster of FIG. 5 demonstrating a connection of the multi-mode sensor to the holster according to an example of the present disclosure.
Figure 7:
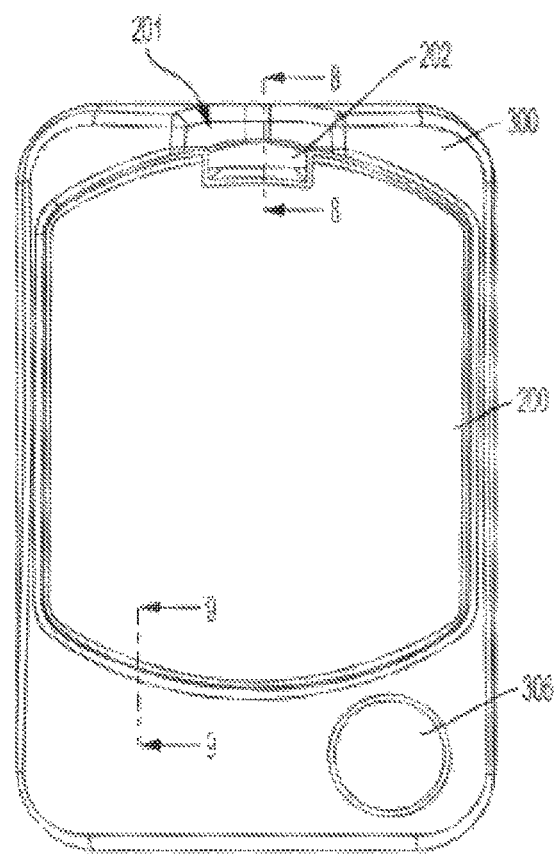
FIG. 7 is a front view of the multi-mode sensor and holster of FIG. 5 when connected.
Figure 8:
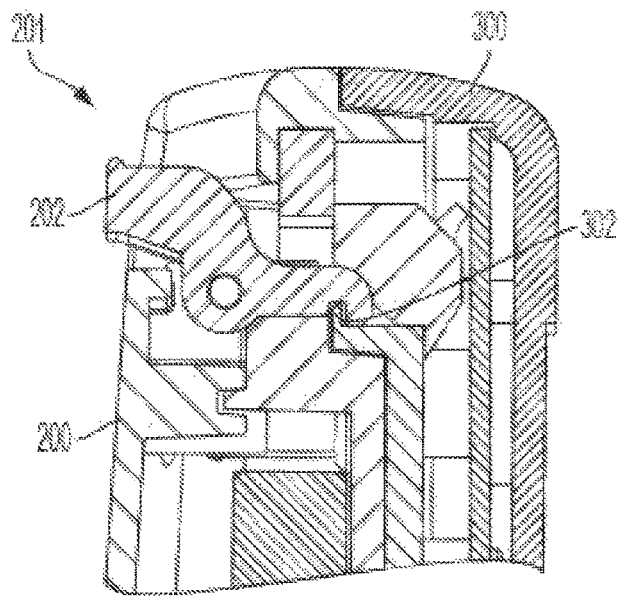
FIG. 8 is a partial cross-sectional view of the multi-mode sensor and holster of FIG. 5 taken along lines 8-8 shown in FIG. 7.
Figure 9:
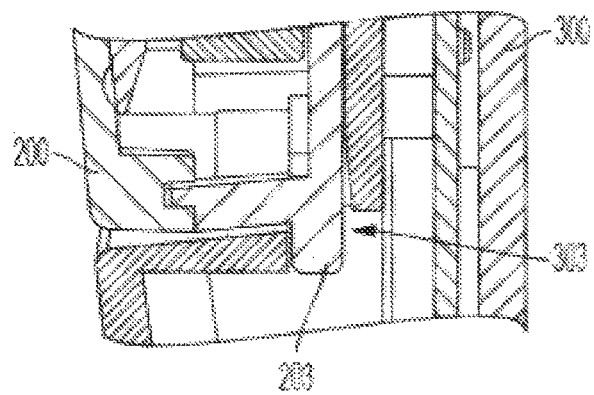
FIG. 9 is a partial cross-sectional view of the multi-mode sensor and holster of FIG. 5 taken along lines 9-9 shown in FIG. 7.
Figure 10:
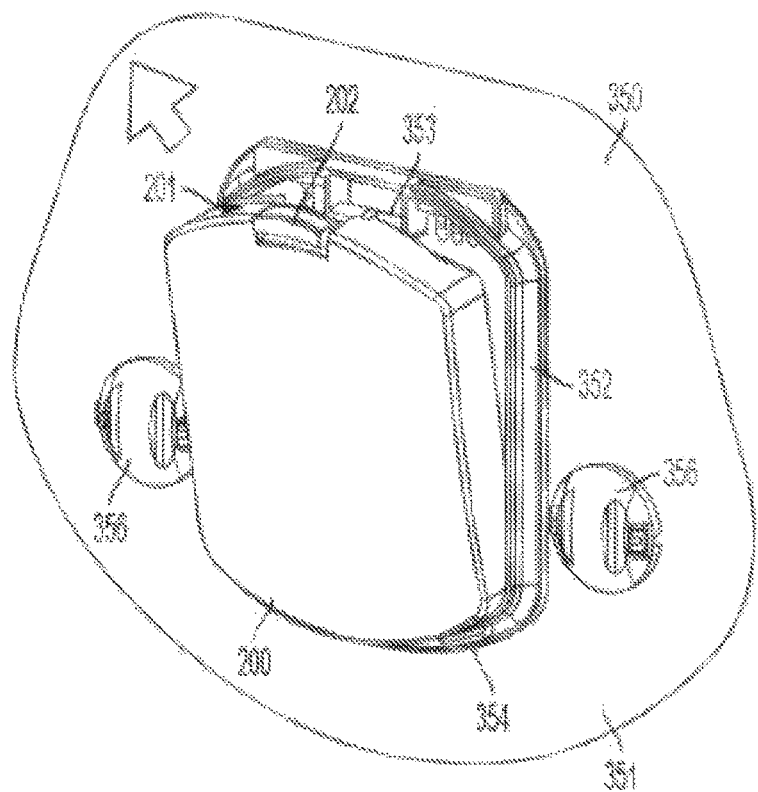
FIG. 10 is a perspective view of a multi-mode sensor and patch of the patient monitoring system of FIGS. 1A-1C according to an example of the present disclosure.
Figure 11:
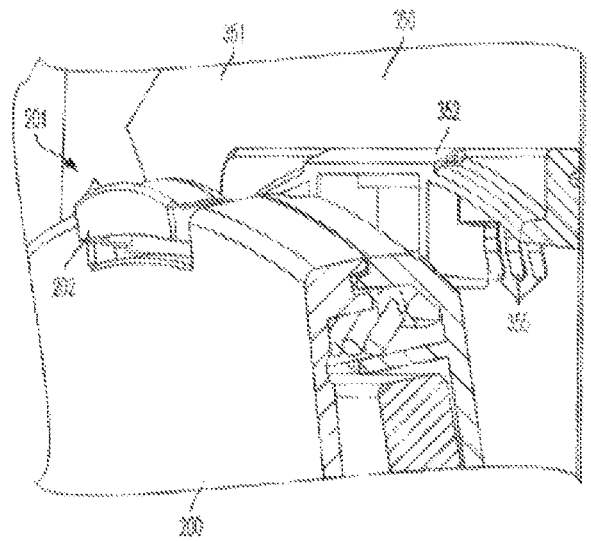
FIG. 11 is an enlarged perspective view of the multi-mode sensor and patch of FIG. 10.
Figure 12:
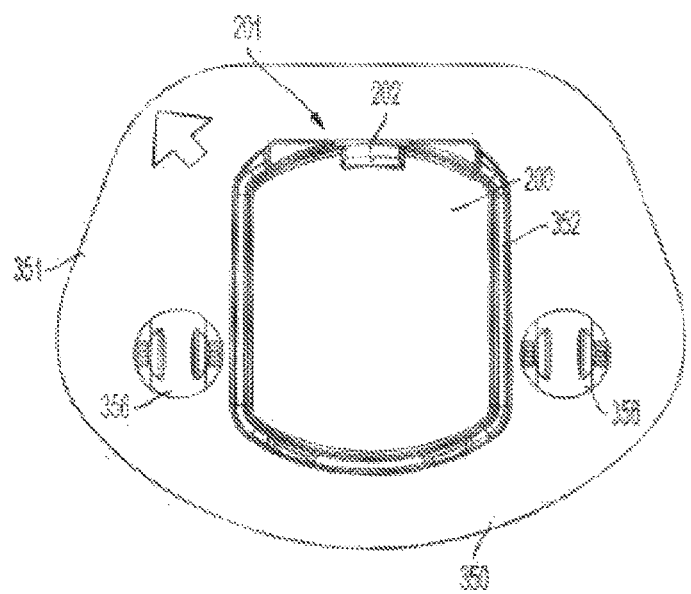
FIG. 12 is a front view of the multi-mode sensor and holster and patch of FIG. 10 when connected.
Figure 17:
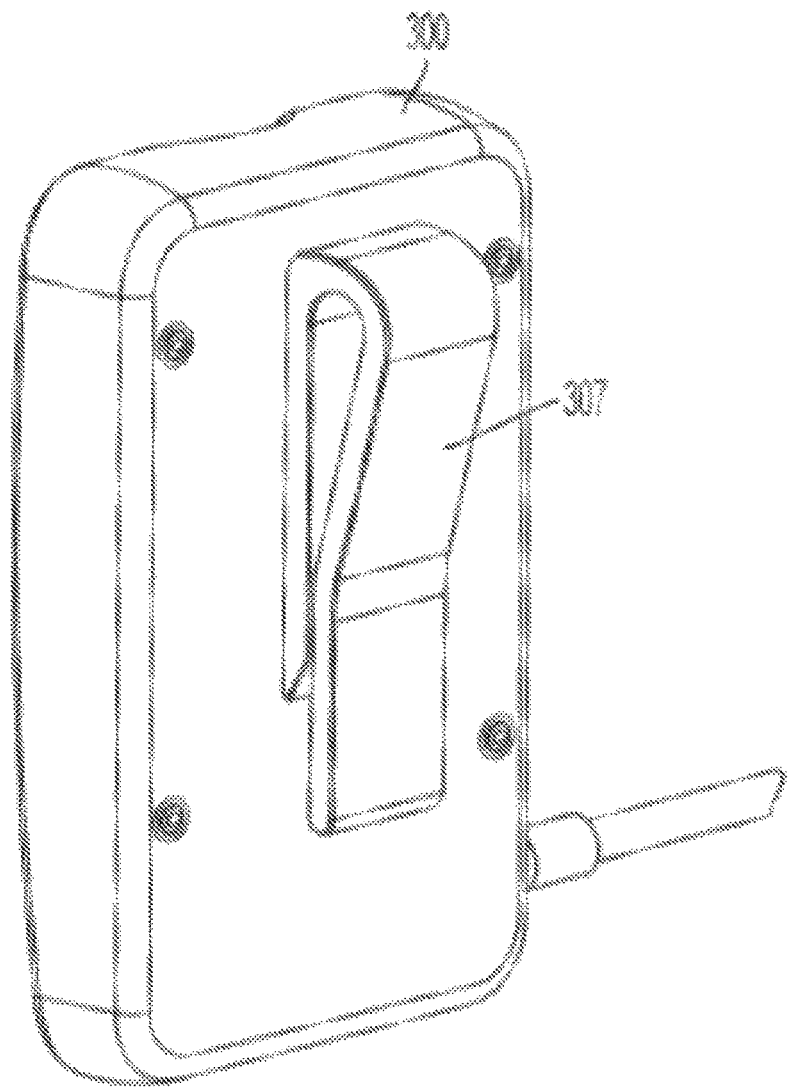
FIG. 17 is a rear perspective view of the holster of FIG. 14 according to an example of the present disclosure.

According to certain examples, the holster 300 may include one or more connection mechanisms configured to removably connect the holster 300 to the patient P. In particular, as shown in FIGS. 6 and 17, the connection mechanism may comprise a clip or belt clip 307 disposed on a rear surface thereof opposite to the multi-mode sensor 200. The clip 307 is configured to connect the holster 300 to an article of the clothing of the patient P, such as a belt, or to a strap or band 309 extending around the arm, leg, or waist of the patient P.

Figure 18:
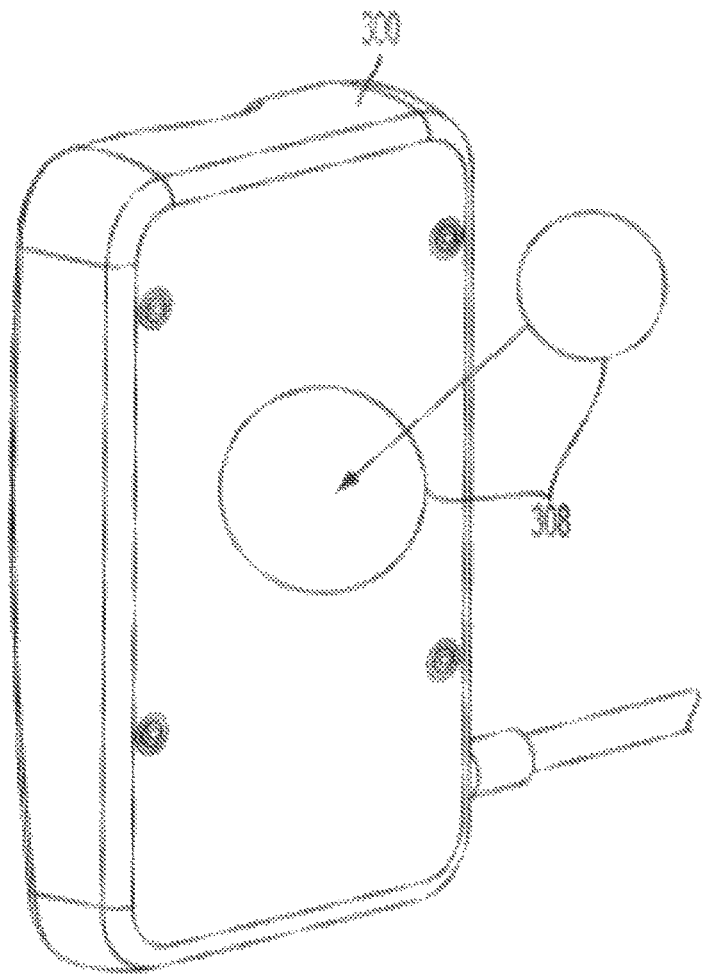
FIG. 18 is a rear perspective view of the holster of FIG. 14 according to another example of the present disclosure.

As shown in FIG. 18, the connection mechanism may comprise a magnetic coupling 308 comprised of a magnet affixed to the rear surface of the holster 300 and a complementary magnet that may be detached from a magnetic engagement with the magnet on the holster 300. The magnetic coupling 308 may be used to connect the holster 300 to an article of clothing of the patient P, such as a shirt, undergarment, or hospital gown, by placing the complementary magnet inside the article of clothing and then magnetically engaging the magnets to each other to hold the holster 300 in place on the article of clothing.

Figure 19:
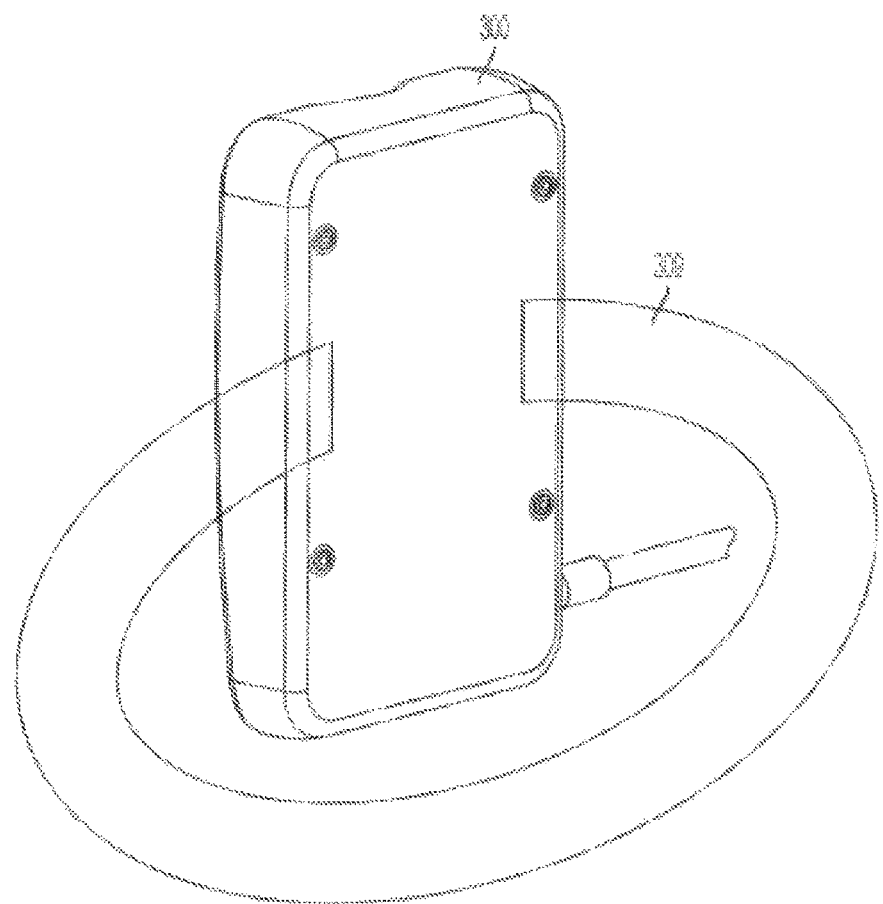
FIG. 19 is a rear perspective view of the holster of FIG. 14 according to another example of the present disclosure.

As shown in FIG. 19, the connection mechanism may comprise the band 309 attached directly to the rear surface of the holster 300. The band 309 may be wrapped around the waist, arm, or leg of the patient P to attach the holster 300 to the body of the patient P. Different sizes and configurations of bands 309 may be used in connection with the holster 300 according to the needs of the patient P for convenience and comfort. For instance, the band 309 may be detachably attached to the holster 300 so that different bands 309 can be interchanged. The band 309 may also include free ends that can be secured together with a buckle or closure so that the band 309 and the holster 300 can be more easily worn and removed by the patient P.

Figure 20:
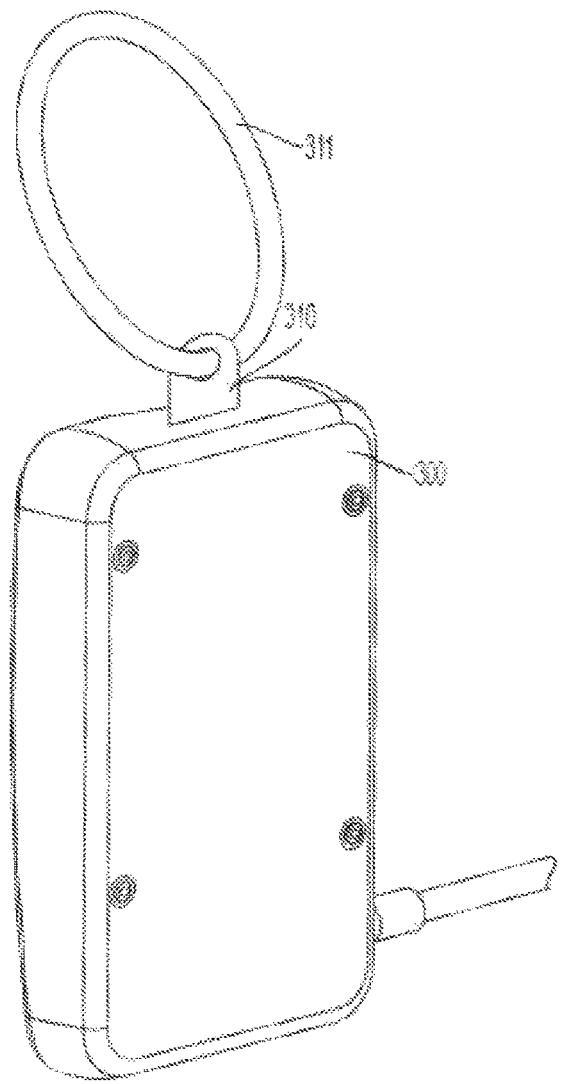
FIG. 20 is a rear perspective view of the holster of FIG. 14 according to another example of the present disclosure.

As shown in FIG. 20, the connection mechanism may comprise an eyelet 310 affixed to an upper end of the holster 300 and a necklace or neck lanyard 311 extending through the eyelet 310 such that the holster 300 may be worn around the neck of the patient P.

It is to be appreciated that the connection mechanism of the holster 300 may be chosen by the physician and the patient P to best suit the needs of the patient P for comfort and convenience with respect to wearing the holster 300 for an extended period of time while minimizing interference with the normal activities of the patient P, including exercise, household tasks, hobbies and activities, and sleeping.

It is also be appreciated that the holster 300 and the connection mechanism can be chosen to facilitate management of the associated monitoring cables 320 connected to the patient P and avoid entanglements with the body and clothing of the patient P or inadvertent disconnection between the cables 320 and the holster 300 or the electrode pads 330. According to one example, the holster 300 may be provided with a specific connection mechanism based on an order from the physician. According to another example, the holster 300 may be provided with multiple connection mechanisms that may then be chosen, interchanged, and reconfigured by the physician and/or the patient P based on the needs of the patient P for comfort and convenience while wearing the holster 300. For instance, the patient P may select the preferred connection mechanism based on the expected activities during the day. The patient P may prefer to use the strap 309 while sleeping or the lanyard 311 while going for a walk or performing errands or the belt clip 307 or magnetic coupling 308 if the patient P prefers to wear the holster 300 in a less conspicuous manner. The multi-mode sensor 200 may be configured to detect the choice of the connection mechanism based on the accelerometer data provided by the 3D accelerometers 258, 322.

According to one example of the present disclosure, the holster 300 may also include one or more user interfaces configured to be actuated by the patient P to allow the patient P to interact with the multi-mode sensor 200 and/or the holster 300 and to provide commands to the multi-mode sensor 200. In particular, the user interface on the holster 300 may include a symptom report button 306 on the front side thereof, which on actuation by the patient P will cause the multi-mode sensor 200 to generate an event report that includes the physiological data acquired by the multi-mode sensor 200 when the symptom report button 306 is actuated by the patient P. The event report may then be transmitted to the multi-mode sensor 200 to the remote location 103 and flagged for attention by the physician or other medical personnel. For instance, if the patient P were to experience an acute symptom such as dizziness, lightheadedness, shortness of breath, palpitations, etc. or were to fall or stumble due to a lack of balance, the patient P could actuate the symptom report button 306 to cause the event report to be generated by the multi-mode sensor 200 and transmitted to the remote location 103 for review/re-transmission to the physician or other medical personnel for review (e.g., to mark a symptomatic period of time) and a determination of whether the patient P requires immediate or expedited medical intervention.

With reference to FIGS. 1B, 2B, 2C, 10-12, and 16, the patient monitoring system 100 includes the patch 350. The patch 350 may comprise an adhesive layer applied to a surface of a fabric base 351 that is configured to be removably attached to the skin of the patient P via the adhesive layer. A housing 352 is disposed on the fabric base 351 and is configured to removably receive the multi-mode sensor 200. The patch 350 may also comprise a plurality of ECG electrodes 356 disposed in or on the fabric base 351. The ECG electrodes 356 are configured to detect ECG signals of the patient P. In particular, the plurality of ECG electrodes 356 disposed in or on the fabric base 351 comprises two ECG electrodes 356. The housing 352 of the patch 350 also includes one or more electrical contacts 355 that can be engaged by corresponding electrical contacts 210 on the multi-mode sensor 200 for placing the multi-mode sensor 200 in communication with the housing 352 and the other components of the patch 350, such as the ECG electrodes 356. The ECG electrodes 356 may be coupled to the multi-mode sensor 200 by dedicated wiring within the patch 350.

The patch 350 may be disposable (e.g., single- or few-use patches), and may be made of biocompatible, non-woven material. Additionally or alternatively, the patch 350 can include a frame onto which the sensor is mechanically affixed. For example, the frame may be ultrasonically welded onto the non-woven material. According to certain examples, the patch 350 is of a type that is configured to be continuously worn by the patient P for an extended period of time (days, weeks, months, years), as discussed above and in United States Patent Application Publication No. 2019/0046038. In particular, according to certain examples of the present disclosure, the extended time period that the patch 350 may be worn by the patient P comprises a period of between around 6 hours and around 5 days, or a period of between around 6 hours and around 10 days, or a period of between around 3 days and around 30 days, or a period of between around 3 days and around 60 days, or a period of between around 3 days and around 90 days. It is to be appreciated that the patch 350 may be configured so as to be worn for any extended period of time found to be suitable to those having ordinary skill in the art. It is also to be appreciated that the multi-mode sensor 200 may be used continuously over a period of days, weeks, months, or years with multiple patches 350 that are replaced at regular intervals according to the example time periods discussed above.

Examples of locations on the surface of the body of a patient P at which a patch 350 may be placed are shown in FIGS. 2B and 2C, where the patch 350 housing the multi-mode sensor 200 is shown as placed at on the side (below armpit, for example) (FIG. 2B) and upper chest (FIG. 2C) of the torso of the patient P. It is to be noted that the patch 350 may be placed on any part of the surface of the body of the patient P that allows for efficient monitoring and recording of a physiological data (e.g., area of skin that allows for uniform attachment of the patch 350 to the skin). For example, one may place the patch 350 under an armpit at the nipple level for obtaining RF-based physiological data.

Figure 16B:
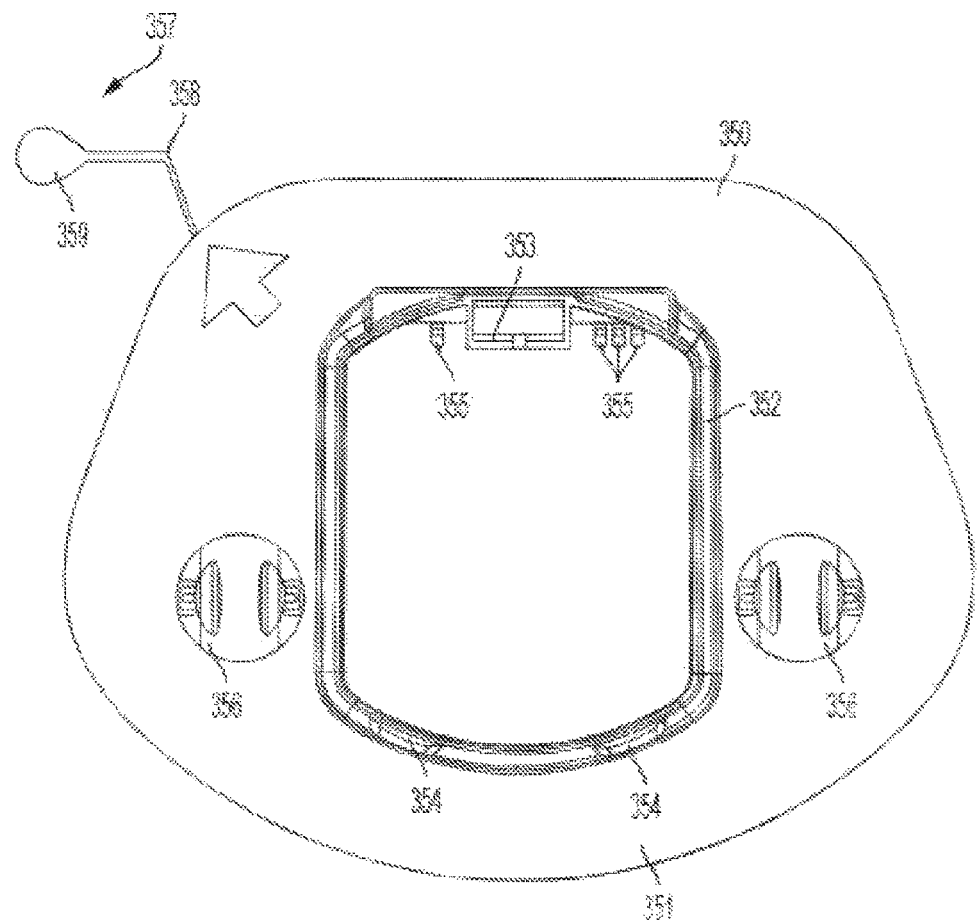
FIG. 16B is a front view of the patch of the patient monitoring system of FIGS. 1A-1C according to another example of the present disclosure.

With reference to FIG. 16B, according to an example of the present disclosure, the patch 350 may also be provided with an extension piece 357; i.e., a "tadpole" mechanically coupled to the patch 350, such as by a cable or wire 358 connected to the patch 350 and/or to the receptacle 352 on the patch 350. The extension piece 357 may have a distal end with an electrode connector 359 incorporated therein that may be connected to an electrode pad 330 containing an ECG electrode, as discussed above. The addition of such an extension piece allows for an additional ECG electrode to be placed at a further distance from the ECG electrodes 356 provided on the patch 350. By increasing the distance between the ECG electrodes in this manner, one is able to obtain an ECG signal that contains more detail than if only two ECG electrodes are utilized (e.g., more prominent p-waves in comparison to the ECG electrodes 356 spaced closely to each other on the patch 350). According to one example, the cable or wire 358 of the extension piece 357 is sufficiently long to reach a location on an opposite side of the body of the patient P from the position of the patch 350. It is to be appreciated that the extension piece 357 may be configured to be positioned anywhere on the body of the patient P distal from the position of the patch 350, such as is shown in FIGS. 2C and 2D, that is suitable for obtaining ECG signals from the patient P in tandem with the electrodes 356 on the patch 350. It is also to be appreciated that the electrode connector 359 may include other sensing components, such as an accelerometer, that may expand the sensing capabilities of the multi-mode sensor 200 when in the patch mode.

With reference to FIGS. 5-14 and 16, as discussed above, the multi-mode sensor 200 comprises the attachment mechanism 201 for removably connecting the multi-mode sensor 200 to the holster 300 or the patch 350. According to certain examples, the holster 300 and the patch 350 include the same features configured to be engaged by the attachment mechanism 201 on the multi-mode sensor 200 so that the multi-mode sensor 200 may be secured on the holster 300 and the patch 350 in the same manner.

According to one example, the attachment mechanism 201 comprises a pivotable latch 202 disposed on the multi-mode sensor 200. The pivotable latch 202 is configured to engage a corresponding catch 302 formed on or in the holster 300 or a corresponding catch 353 formed on or in the housing 352 of the patch 350. The attachment mechanism 201 may also comprise at least one rib 203 disposed on the multi-mode sensor 200. The at least one rib 203 is configured to be received in a corresponding recess 303 defined in the receiver 301 of the holster 300 or recess 354 defined in the housing 352 of the patch 350. According to one example, the multi-mode sensor 200 comprises two ribs 203, and the receiver 301 of the holster 300 and the housing 352 of the patch 350 each comprise two corresponding recesses 303, 354.

As shown in FIGS. 5-11, the multi-mode sensor 200 may be connected to the holster 300 or the housing 352 of the patch 350 by aligning the ribs 203 on the multi-mode sensor 200 with the corresponding recesses 303, 354 in the holster 300 or the housing 352 of the patch 350 and inserting the ribs 203 into the recesses 303, 354. The multi-mode sensor 200 can then be pivoted into the receiver 301 of the holster 300 or the housing 352 of the patch 350 until the pivotable latch 202 comes into engagement with the corresponding catch 302, 353 on the holster 300 and the housing 352 of the patch 350. The receiver 301 of the holster 300 and the housing 352 of the patch 350 are configured to position the multi-mode sensor 200 such that the electrical contacts 210 on the multi-mode sensor 200 come into engagement with the corresponding electrical contacts 304, 355 on the holster 300 and the patch 350.

According to one example of the present disclosure, attachment mechanism 201 forms a snap connection between the multi-mode sensor 200 and the holster 300 or the patch 350. In particular, the pivotable latch 202 may include an internal biasing mechanism, such as a torsion spring, the biases the latch 202 to a latching position. The latch 202 includes a handle end disposed toward the outer side of the multi-mode sensor 200, i.e., the side configured to face away from the holster 300 or patch 350, which is configured to be handled by the patient P or other person handling the multi-mode sensor 200. The latch 202 also includes an opposite catch end disposed toward the inner side of the multi-mode sensor 200, i.e., the side configured to face toward the holster 300 or patch 350, which is configured to engage the corresponding catch 302, 353. When the pivotable latch 202 comes into engagement with the catch 302, 353, the catch end of the pivotable latch 202 will snap into place over the catch 302, 353 producing a "snap" or "click" that may be heard or felt by the patient P when inserting the multi-mode sensor 200 into the holster 300 or the patch 350. The patient P can also view the position of the handle end of the pivotable latch 202 to see that the pivotable latch 202 has moved into the latched position. Accordingly, the attachment mechanism 201 can produce visual, audible, and tactile feedback indicating that the multi-mode sensor 200 has been correctly positioned within the holster 300 or the housing 352 of the patch 350.

With reference to FIG. 1C, as discussed above, the patient monitoring system 100 may comprise the support garment 20 and electrode assembly 10, in accordance with one example of the present disclosure. The device of FIG. 1C can include a wearable cardioverter defibrillator (WCD) device, further comprising a WCD controller 400 comprising circuitry for analyzing ECG, detecting treatable arrhythmias (e.g., ventricular tachycardia, ventricular fibrillation, bradycardia, tachycardia, asystole, etc.) and initiating an appropriate treatment (e.g., defibrillation, cardioversion, and pacing, among others). The electrode assembly 10 comprises a number of monitoring/sensing electrodes 12 worn by the patient P so as to be in contact with the skin of the patient P. According to one example, the monitoring/sensing electrodes 12 can be configured to receive ECG signals from the patient P. The electrode assembly 10 may further incorporate a vibration box 13 connected by wires to the sensing electrodes 12. The vibration box 13 may be utilized to provide the patient P with a tactile alarm that the sensing electrodes 12 and/or the therapy electrodes are not in proper contact with the skin of the patient P. The electrode assembly 10 can be removably coupled to the WCD controller 400. A multi-mode sensor 200 can be included in one or more predetermined locations of the support garment 20, as shown in FIG. 1C.

In accordance with one or more examples, a support garment 20 is provided to keep the electrodes 12 in place against the body of the patient P while remaining comfortable during wear. Such an example support garment is described in United States Patent Application Publication No. 2012/0283794, the content of which is incorporated by reference in its entirety.

In order to obtain a reliable ECG signal so that the multi-mode sensor 200 can function effectively and reliably, the sensing electrodes 12 must be in the proper position and in good contact with the skin of the patient P. The electrodes 12 need to remain in a certain position and not move excessively or lift off the skin's surface. If there is movement or lifting, the ECG signal will be adversely affected with noise and can cause problems with the detection system and in the monitoring system.

In accordance with one or more examples, the support garment 20 may provide comfort and functionality under circumstances of human body dynamics, such as bending, twisting, rotation of the upper thorax, semi-reclining, and lying down. These are also positions that a patient P may assume if he/she were to become unconscious due to an arrhythmic episode. The design of the garment 20 is generally such that it minimizes bulk, weight, and undesired concentrations of force or pressure while providing the necessary radial forces upon the sensing electrodes 12 to ensure device functionality.

As shown in FIG. 1C, the support garment 20 may be provided in the form of a vest or harness having back portion 21 and sides extending around the front of the patient P to form a belt 22. The ends of the belt 22 are connected at the front of the patient P by a closure 31, which may comprise one or more clasps. Multiple corresponding closures 31 may be provided along the length of the belt 22 to allow for adjustment in the size of the secured belt 22 in order to provide a more customized fit to the patient P. It is to be appreciated that the closure 31 may be of any type known to be suitable to those having ordinary skill in the art, such as a clasp, zipper, corresponding hook-and-pile fasteners, buttons, or snaps. The support garment 20 may further include two straps 23 connecting the back portion 21 to the belt 22 at the front of the patient P. The straps 23 have an adjustable size to provide a more customized fit to the patient P. The straps 23 may be provided with sliders 24 to allow for the size adjustment of the straps 23. The straps 23 may also be selectively attached to the belt 22 at the front of the patient P. The back portion 21 and the belt 22 of the support garment 20 may further incorporate attachment points 27 for supporting the sensing electrodes 12 in positions against the skin of the patient P in spaced locations around the circumference of the chest of the patient P. The attachment points 27 may include hook-and-pile fasteners for attaching electrodes 12 having a corresponding fastener disposed thereon to the inside surface of the belt 22. The attachment points 27 may be color coded to provide guidance for appropriately connecting the sensing electrodes 12 to the support garment 20. The support garment 20 may further be provided with a flap 28 extending from the back portion 21. The flap 28 and the back portion 21 include snap fasteners 29 for connecting the flap 28 to the inside surface of the back portion 21 in order to define a pouch or pocket for holding the vibration box 13.

The support garment 20 may be comprised of an elastic, low spring rate material that stretches appropriately to keep the electrodes 12 in place against the skin of the patient P while the patient P moves and that is lightweight and breathable. For example, the support garment 20 may have elastic, low spring rate material composition based on a fiber content of about 20% elastic fiber, 32% polyester fiber, and up to 48% or more of nylon or other fiber. Appropriate materials for the support garment 20 are discussed in detail in the above-mentioned United States Patent Application Publication No. 2012/0283794.

According to certain examples, the support garment 20 may incorporate a clip, fastener, a hook-and-loop fastener, or another mechanism similar to the above-mentioned holder 352 provided on the patch 350 for positioning the multi-mode sensor 200 on the support garment 20 and placing the multi-mode sensor 200 in communication with the electrode assembly 10. For example, in embodiments wherein the multi-mode sensor 200 includes RF antennas disposed on an underside (e.g., skin-facing side) of the housing of the sensor 200, the sensor 200 is to be positioned as close as possible to the skin of the patient P. Such positioning is needed for operation of the RF modules in the sensor 200. For example, on the side of the housing of the sensor 200 facing away from the skin of the patient P, a clip or hook-and-loop fastener may be configured to engage with a corresponding holder or hook-and-loop fastener disposed at a predetermined location on the support garment 20. For example, the predetermined location can be selected such that the sensor 200 is positioned along a left midaxillary line in line with the nipple (side location) and along the left midclavicular line, above the nipple and below the clavicle. In an example, in addition or alternatively, the sensor 200 can be positioned on a chest and/or abdomen area (e.g., front and lateral locations). The elasticity of the support garment 20 can hold the sensor 200 in place and prevent excessive side-to-side motion due to patient movement.

In some examples, the sensor 200 may not include an RF module and may be configured to monitor ECG along with posture, activity, and respiration only. According to such examples, the sensor 200 need not be mounted close to the skin of the patient P. In such examples, the support garment 20 is provided in combination with the holster 300 worn separately by the patient P, and a first connector end of the electrode assembly 10 is connected to the holster 300 in the manner discussed above with respect to the monitoring cable assembly. A second connector end of the electrode assembly 10 can be removably connected to a WCD controller 400 as described above. Alternatively, in some examples, the WCD controller 400 may incorporate a clip, fastener, or other attachment mechanism similar to the above-mentioned holder 252 for positioning the multi-mode sensor 200 in communication with the electrode assembly 10. Accordingly, the support garment 20 may serve as an alternative to the electrode pads 330 for holding the ECG electrodes 12 against the skin of the patient P while the multi-mode sensor 200 collects physiological data in the holster mode. Alternatively, as discussed above, the configuration circuitry 251 of the multi-mode sensor 200 may be configured to determine when the multi-mode sensor 200 is removably connected to the electrode assembly 10 and the support garment 20 and to cause the multi-mode sensor 200 to acquire the physiological data in a garment mode when connected to the support garment 20. The multi-mode sensor 200 may operate differently in the garment mode due to the differences in configuration between the electrode assembly 10 on the support garment 20 and the monitoring cable assembly discussed above and the positioning of ECG electrodes on the body of the patient P.

According to another example, the multi-mode sensor 200 may be used in combination with a treatment device also associated with the support garment 20 and electrode assembly, such as a wearable defibrillator of the type discussed in the above-mentioned United States Patent Application Publication No. 2012/0283794. The electrode assembly 10 may further incorporate one or more therapy electrodes of the type discussed in the above-mentioned United States Patent Application Publication No. 2012/0283794. The inside surface of the support garment 20 may also include pockets 25, 26 for supporting additional components of the patient monitoring system 100 or components of a separate patient treatment system of the type discussed in the above-mentioned United States Patent Application Publication No. 2012/0283794.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or will be able to ascertain using no more than routine experimentation, many equivalents to the specific inventive embodiments described herein. It is therefore to be understood that the foregoing embodiments are presented by way of example only and that within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined; i.e., elements that are conjunctively present in some cases and disjunctively present in other cases. Multiple elements listed with "and/or" should be construed in the same fashion; i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising", can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive; i.e., the inclusion of at least one, but also including more than one, of a number or list of elements, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, such as "either", "one of", "only one of", or "exactly one of". "Consisting essentially of", when used in the claims, shall have its ordinary meaning as used in the field of patent law.

As used herein in the specification and in the claims, the phrase "at least one", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B", or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising", "including", "carrying", "having", "containing", "involving", "holding", "composed of", and the like are to be understood to be open ended; i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A patient monitoring system for use in either a patch mode or a holster mode for monitoring physiological data of a patient, comprising:
   a multi-mode sensor configured to continuously and/or intermittently acquire the physiological data from the patient in at least two modes comprising the patch mode and the holster mode and to transmit the acquired physiological data to a remote location and/or record the acquired physiological data in an internal memory, the physiological data comprising one or more of patient electrocardiogram (ECG) data, patient posture, patient movement, radio-frequency (RF) based physiological data, body temperature, and/or patient respiration;
   an attachment mechanism disposed on the multi-mode sensor, the attachment mechanism configured to removably connect the multi-mode sensor to either a holster and associated monitoring cables worn by the patient or a patch worn by the patient;
   at least one electrical contact disposed on the multi-mode sensor, the at least one electrical contact configured to engage a counterpart electrical contact of the holster and/or a counterpart electrical contact of the patch; and
   configuration circuitry disposed in the multi-mode sensor, the configuration circuitry configured to:
      determine when the multi-mode sensor is removably connected to the holster, and cause the multi-mode sensor to acquire the physiological data in the holster mode when connected to the holster; and
      determine when the multi-mode sensor is removably connected to the patch, and cause the multi-mode sensor to acquire the physiological data in the patch mode when connected to the patch,
   wherein the configuration circuitry comprises resistance detection circuitry configured to detect a resistance level between the at least one electrical contact of the multi-mode sensor and the counterpart electrical contact of the holster or the counterpart electrical contact of the patch, the configuration circuitry being configured to determine when the multi-mode sensor is removably connected to the holster or the patch based on the detected resistance level.

2. The patient monitoring system according to claim 1, further comprising the holster, the holster configured to removably receive the multi-mode sensor.

3. The patient monitoring system according to claim 2, wherein the holster comprises user interface element configured to be actuated by the patient.

4. The patient monitoring system according to claim 1, further comprising the associated monitoring cables, the associated monitoring cables comprising a plurality of separate cables comprising distal and opposing ends.

5. The patient monitoring system according to claim 4, wherein each of the distal ends of the plurality of separate cables comprises an accelerometer and associated circuitry and the multi-mode sensor is configured to monitor for at least one of: patient posture, patient movement, and/or patient respiration, based on accelerometer data.

6. The patient monitoring system according to claim 1, further comprising the patch, the patch comprising:
   an adhesive layer;
   a fabric base configured to be removably attached to the patient's skin via the adhesive layer;
   a housing configured to removably receive the multi-mode sensor disposed on the fabric base; and
   a plurality of ECG electrodes disposed in or on the fabric base, the plurality of ECG electrodes configured to detect ECG signals of the patient.

7. The patient monitoring system according to claim 6, wherein the plurality of ECG electrodes disposed in or on the fabric base comprises two ECG electrodes.

8. The patient monitoring system according to claim 6, wherein the patch is configured to be continuously worn by the patient for an extended period of time.

9. The patient monitoring system according to claim 1, wherein the multi-mode sensor further comprises at least one radio-frequency (RF) antenna disposed on a patient-facing side of the multi-mode sensor, the at least one RF antenna being configured to transmit RF waves from the multi-mode sensor into the patient and to receive reflected RF waves from the patient.

10. The patient monitoring system according to claim 1, wherein the attachment mechanism comprises one of: a pivotable latch disposed on the multi-mode sensor, the pivotable latch configured to engage a corresponding catch formed on the holster or on the patch; or at least one rib disposed on the multi-mode sensor, the at least one rib configured to be received in a corresponding recess defined in the holster or on the patch.

11. The patient monitoring system according to claim 1, wherein the at least one electrical contact of the multi-mode sensor comprises a plurality of electrical contacts.

12. The patient monitoring system according to claim 11, wherein the plurality of electrical contacts comprises at least one electrical contact configured to communicate ECG data, at least one electrical contact configured to communicate accelerometer data, at least one electrical contact configured to transmit power, and at least one electrical contact configured to transmit an RF signal and/or communicate RF-based physiological data.

13. The patient monitoring system according to claim 1, wherein multi-mode sensor comprises communications circuitry configured to transmit the acquired physiological data to the remote location via one of: a local communications gateway or a cellular telecommunications signal.

14. The patient monitoring system according to claim 1, wherein the multi-mode sensor comprises ECG circuitry configured to communicate with at least one ECG channel and continuously acquire ECG data from the patient.

15. The patient monitoring system according to claim 1, wherein the physiological data comprises RF-based physiological data, and the multi-mode sensor comprises RF circuitry configured to acquire the RF-based physiological data from the patient when in the patch mode.

16. The patient monitoring system according to claim 1, wherein the multi-mode sensor is configured to transmit at least one of: ECG data based on one or more ECG channels to the remote location; and RF-based physiological data to the remote location.

17. The patient monitoring system according to claim 1, wherein the configuration circuitry is configured to determine when the multi-mode sensor is removably connected to a garment, and cause the multi-mode sensor to acquire the physiological data in a garment mode when connected to the garment.

18. The patient monitoring system according to claim 1, wherein the configuration circuitry is configured to determine when the multi-mode sensor is removably connected to a charger device, and cause a battery of the multi-mode sensor to be charged.

19. The patient monitoring system according to claim 1, wherein the multi-mode sensor comprises diagnostic circuitry configured to detect a physiological condition of the patient based on the acquired physiological data.

* * * * *